United States Patent
Malaise et al.

(10) Patent No.: US 11,047,856 B2
(45) Date of Patent: Jun. 29, 2021

(54) METHOD OF EARLY DIAGNOSIS OF IMMUNE-MEDIATED INFLAMMATORY DISEASE

(71) Applicants: UNIVERSITE DE LIEGE, Angleur (BE); CENTRE HOSPITALIER UNIVERSITAIRE DE LIEGE, Liege (BE)

(72) Inventors: Michel Malaise, Liege (BE); Dominique De Seny, Liege (BE)

(73) Assignees: UNIVERSITE DE LIEGE, Angleur (BE); CENTRE HOSPITALIER UNIVERSITAIRE DE LIEGE, Liege (BE)

( * ) Notice: Subject to any disclaimer, the term of this patent is extended or adjusted under 35 U.S.C. 154(b) by 153 days.

(21) Appl. No.: 16/314,654

(22) PCT Filed: Jun. 23, 2017

(86) PCT No.: PCT/EP2017/065591
§ 371 (c)(1),
(2) Date: Dec. 31, 2018

(87) PCT Pub. No.: WO2018/007173
PCT Pub. Date: Jan. 11, 2018

(65) Prior Publication Data
US 2019/0317091 A1 Oct. 17, 2019

(30) Foreign Application Priority Data
Jul. 2, 2016 (EP) .................................... 16177673

(51) Int. Cl.
*G01N 33/564* (2006.01)
*G01N 33/68* (2006.01)

(52) U.S. Cl.
CPC ....... *G01N 33/564* (2013.01); *G01N 33/6848* (2013.01); *G01N 2800/105* (2013.01)

(58) Field of Classification Search
None
See application file for complete search history.

(56) References Cited

U.S. PATENT DOCUMENTS 8,494,818 B2   7/2013   Hubert et al.

FOREIGN PATENT DOCUMENTS

WO   WO-2012/104624 A2   8/2012

OTHER PUBLICATIONS

Percy, A.J. et al., Comparison of standard- and nano-flow liquid chromatography platforms for MRM-based quantitation of putative plasma biomarker proteins, Analytical Bioanalytical Chemistry, 404, 1089-1101 (Year: 2012).*

(Continued)

*Primary Examiner* — Xiaoyun R Xu
(74) *Attorney, Agent, or Firm* — Foley & Lardner LLP

(57) ABSTRACT

An in-vitro method for early diagnosing or prediction of immune-mediated inflammatory diseases, comprising: —obtaining a sample from a subject; —quantifying simultaneously by one LC/MS-MS analysis of said sample, a presence of V65 vitronectin fragment or fragment, variant or degradation product thereof; and a presence of a complement C3f or fragment or variant or degradation products thereof.

18 Claims, 18 Drawing Sheets
Specification includes a Sequence Listing.

A. C3f - MS spectra

B. Vitronectin fragment - MS spectra

(56) References Cited

OTHER PUBLICATIONS

Xiang, Y. et al. Comprehensive Investigation of Disease-Specific Short Peptides in Sera From Patients With Systemic Sclerosis, Complement C3f-des-arginine, Detected Predominantly in Systemic Sclerosis Sera, Enhances Proliferation of Vascular Endothelial Cells. Arthriris & Rheumatism, 56(6), 2018-2030 (Year: 2007).*

International Search Report and Written Opinion dated Sep. 14, 2017, from application No. PCT/EP2017/065591.

B.K. Matuszewski et al., "Strategies for the Assessment of Matrix Effect in Quantitative Bioanalytical Methods Based on HPLC-MS/MS" Analytical Chemistry, vol. 75, Issue 13, Jun. 4, 2003, pp. 3019-3030.

Cobraiville, Gaël et al, "Validation of a new method by nano-liquid chromatography on chip tandem mass spectrometry for combined quantitation of C3f and the V65 vitronectin fragment as biomarkers of diagnosis and severity of osteoarthritis", TALANTA, vol. 169, Mar. 28, 2017, pp. 170-180.

De Seny Dominique et al, "Discovery and biochemical characterisation of four novel biomarkers for osteoarthritis", Annals of the Rheumatic, vol. 70, Jun. 1, 2011, pp. 1144-1152.

Gosetti, Fabio et al., "Signal suppression/enhancement in high-performance liquid chromatography tandem mass spectrometry" Journal of Chromatography A, vol. 1217, Issue 25, Jun. 18, 2010, pp. 3929-3937.

Gonzalez-Iglesias, Hector et al, "Validation of Candidate Glaucoma Biomarkers by Quantitative Proteomics", Investigative Ophthalmology & Visual Science—IOVS, Association for Research in Vision and Ophthalmology, US, vol. 56, No. 7, Jun. 1, p. 3676.

JH Kellgren et al., "Radiological assessment of osteo-arthrosis", Annals of the Rheumatic Diseases, vol. 16, Issue 4, Dec. 1957, pp. 494-502.

Paul J. Taylor, "Matrix effects: the Achilles heel of quantitative high-performance liquid chromatography-electrospray-tandem mass spectrometry", Clinical Biochemistry, vol. 38, Issue 4, Apr. 2005, pp. 328-334.

V. Houbart et al., "Development of a nano-liquid chromatography on chip tandem mass spectrometry method for high-sensitivity hepcidin quantitation", Journal of Chromatography A, vol. 1218, Issue 50, Dec. 16, 2011, pp. 9046-9054.

V. Houbart et al., "Influence of sample and mobile phase composition on peptide retention behaviour and sensitivity in reversed-phase liquid chromatography/mass spectrometry", Journal of Chromatography A, vol. 1314, Nov. 2013, pp. 199-207.

* cited by examiner

A. C3f - MS spectra

B. Vitronectin fragment - MS spectra

C. C3f - MS/MS spectra

D. Vitronectin fragment - MS/MS spectra

E. C3f – unlabeled and labeled peptides

F. Vitronectin fragment – unlabeled and labeled peptides

| | | C3f | Vitro frag. |
|---|---|---|---|
| Process Efficiency (PE) | c/a | 173.7 | 115.2 |
| Matrix Effects (ME) | b/a | 193.0 | 111.6 |
| Extraction Recovery (ER) | c/b | 90.0 | 103.2 |
| Extraction Yield (EY) | d/a | 226.8 | 147.0 |

A. C3f – SELDI

B. Vitronectin fragment - SELDI

C. C3f – LC-chip-MS

D. Vitronectin fragment – LC-chip-MS

E. C3f – SELDI *vs* LC-chip-MS

| | |
|---|---|
| Spearman r: | 0.53 |
| 95% confidence interval: | 0.38 to 0.65 |
| P value (two-tailed): | < 0.0001 |
| P value summary: | *** |
| Slope: | 8.722 ± 0.8616 |
| Y-intercept when X=0: | -3.398 ± 3.991 |
| X-intercept: | 0.3895 |

F. Vitronectin fragment – SELDI *vs* LC-chip-MS

| | |
|---|---|
| Spearman r: | 0.64 |
| 95% confidence interval: | 0.38 to 0.65 |
| P value (two-tailed): | < 0.0001 |
| P value summary: | *** |
| Slope: | 0.6185 ± 0.1588 |
| Y-intercept when X=0 | 5.178 ± 2,037 |
| X-intercept: | 8.371 |

SEQUENCE LISTING

```
<160> NUMBER OF SEQ ID NOS: 2

<210> SEQ ID NO 1
<211> LENGTH: 17
<212> TYPE: PRT
<213> ORGANISM: human

<400> SEQUENCE: 1

Ser Gln Arg Gly His Ser Arg Gly Arg Asn Gln Asn Ser Arg Arg Pro
1               5                   10                  15

Ser

<210> SEQ ID NO 2
<211> LENGTH: 17
<212> TYPE: PRT
<213> ORGANISM: human

<400> SEQUENCE: 2

Ser Ser Lys Ile Thr His Arg Ile His Trp Glu Ser Ala Ser Leu Leu
1               5                   10                  15

Arg
```

METHOD OF EARLY DIAGNOSIS OF IMMUNE-MEDIATED INFLAMMATORY DISEASE

RELATED APPLICATIONS

The present application claims priority under 37 U.S.C. § 371 to International Patent Application No. PCT/EP2017/065591, filed Jun. 23, 2017, which claims priority to and the benefit of European Patent Application No. 16177673.7, filed on Jul. 2, 2016. The contents of these applications are hereby incorporated by reference in their entireties.

The present invention relates to a method of diagnosing early-stage Immune-mediated inflammatory diseases, particularly osteoarthritis.

BACKGROUND OF THE INVENTION

Immune-mediated inflammatory disease (IMID) is a concept used to describe a group of diseases whose etiology remains unknown but that are characterized by common inflammatory pathways. IMIDs may result from, or be triggered by, a dysregulation of the normal immune response. Disorders as diverse as rheumatoid arthritis (RA), crohn's disease, asthma, ankylosing spondylitis (AS), systemic lupus erythematosus, sclerodermia, osteoarthritis and others belong to IMIDs and may affect any organ system, resulting in significant morbidity, reduced quality of life and premature death. The incidence of IMIDs in Western society approximates 5-7%.

Osteoarthritis (OA) is one of the most common chronic joint diseases belonging to IMID that is responsible for substantial health deficits, disability to work and public health cost. Further, OA is becoming increasingly more prevalent as the population ages. Osteoarthritis is mainly characterized by a dysregulation of normal joint homeostasis that leads to intra-articular cartilage degradation, attempted repair and inflammation mediated by cytokines and growth factor. Recently, OA lost its qualification of a degenerative disease to become a metabolic disorder. The accepted paradigm until now was that OA synovitis was pauci-cellular, non-inflammatory and avascular, almost similar to normal synovium. But recent studies on synovial biopsies have highlighted a marked role of innate immunity in OA with the presence of "inner DAMPS" (inner Damage Associated Molecular Patterns) and "outer PAMPS" (outer Pathogen Associated Molecular Patterns) interacting with toll-like receptors. An inflammatory synovitis was also described with features such as synovial proliferation, subintimal macrophages and lymphocytes infiltration and neovascularization. Accordingly, OA was classified as an IMID disorder. Osteoarthritis management is one of the major socioeconomic issues, and the development of methods to diagnose and assess the severity and progression of OA is a major goal in the arthritis research community. Diagnosis depends on patient-reported pain and disability, followed by imaging (usually plain X-ray) and blood biochemistry to rule out any other rheumatic diseases such as RA.

In the early stage of OA, cartilage starts to become soft with swelling. Proteoglycan overexpression enhances harmful cartilage hyper-hydration leading to cartilage breakdown and collagen fibers dissociation. Catabolic hyperactivity of chondrocytes is observed. The synovial membrane starts to secrete inflammatory mediators (cytokines and metalloproteinases) enhancing extracellular matrix degradation in cartilage and releasing cleaved fragments of proteins inside the joint cavity.

At an advanced stage, the destruction wins the deeper layers exposing the subchondral bone. Neovascularization occurs inside the cartilage.

Rheumatoid arthritis (RA) is another arthritis pathology affecting joints but presenting autoimmune and systemic inflammatory properties while OA is primarily presenting a local inflammation in joints. RA is difficult to diagnose in its early stages because the early symptoms mimic those of any other diseases. No accurate method is available. At a late stage imaging tests allow to follow the progression of RA over time. A C-reactive protein (CRP) test is also used to indicate the presence of an inflammatory process.

Systemic lupus erythematosus (SLE) is another immune-mediated inflammatory disease with a complex multifactorial aetiology, mostly affecting women aged 16-45 years old, characterized by inflammation of immune origin of many organs (systemic disease) and subject to many exacerbations and remissions. In addition, the disease is also characterized by the presence of autoantibody mostly against cell nucleus components detectable for example at the serum level. In our countries, prevalence is about 10-60/100,000 and incidence 2-4/100,000/year. The pathogenicity is complex involving a hyperactivity of the cellular and humoral immune system leading to direct cell-driven damages, production of cytotoxic autoantibodies and non-specific deposits of circulating immune complexes. IL-10 is overproduced by many cells (Th2, B, monocytes, keratinocytes and placental cells). In addition to various genetic factors including congenital deficiency in C4 component, SLE is triggered by exposure to ultraviolet rays and exposure to estrogens. Inaugural manifestations mostly invariably affect the musculo skeletal system and the skin. Throughout the evolution, joints are affected in about 90% of the cases, the skin in 70%, the haemopoietic system in 65%, the lung and heart (pleuritis and pericarditis) in 60%, the kidneys in 50%, the vessels in 20% and the central nervous system in 15%. Biological tests are characterized by a hallmark presence of antinuclear antibodies (sensitivity 99%, specificity 67%) and anti-double strand anti-DNA antibodies (sensitivity 40-75%, specificity 95%) or anti-Sm antibodies (sensitivity 10-20%, specificity 100%). Raising levels of anti-DNA antibodies and serum hypocomplementemia are worsening factors predicting clinical flares. When unknown, SLE may be discovered through frequent fetal loss mainly due to the presence of anti-phospholipid antibodies leading to thrombosis of the placental vessels. And a pregnancy can induce severe disease flares in uncontrolled SLE. Here again SLE is difficult to diagnose because of its complex multifactorial aetiology. A positive test for antinuclear antibody is not enough to identify the immune-mediated disease. No test is available in the art to detect SLE at an early stage.

Sclerodermia is another and severe auto-immune disease of unknown origin characterized pathologically by a dysregulation of the production of components of the connective tissue, leading to an overproduction notably of collagen in various organs driving an irreversible fibrosis. In addition, there exists widespread vascular damage with an endothelial dysfunction leading microvascular obliteration. Lastly, one observes tissue infiltration of mononuclear inflammatory cells often in a perivascular distribution. The prevalence is about 2-5/100,000 and the incidence 5-10/106/an. The sex ratio is 4 females/1 male and the disease occurs mostly after 40 years. If a genetic contribution is recognized, the most hallmark is a major role for enviromental agents such as silica, vinil chloride, toxic oil (alinine-treated rapeseed oil), and some drugs as bleomycin, pentazocine and L-5-hydroxytrytophan. The disease is mimicked in chronic graftversus-host disease. The most targets for the immune cells are endothelial cells and the fibroblasts that transform into myofibroblasts. There are several evidence for a major role of TGF-β, PDGF, endothelin and various integrins. Two main clinical forms exist: the diffuse cutaneous systemic sclerosis (dcSSc) and the limited cutaneous systemic sclerosis (lcSSc). In dcSSc, the onset of skin changes (puffy or hidebound) within 1 year of onset of Raynaud phenomena (white finger). There is truncal and acral skin involvement, presence of tendon friction rub, early and significant incidence of interstitial lung disease, oliguric renal failure, diffuse gastrointestinal disease, and myocardial involvement. At capillaroscopy, one sees naifold capillary dilatation and capillary destruction. Antinuclear antibodies are present in 100%, with a characteristic nucleolar pattern (40%). Antitopoisomerase I antibody (Scl70) is found in 30% of patients. In lcSSc, Raynaud phenomena occurs usually for years (decade) and the skin involvement is limited to hands, face, feet and forearms (acral). There is a significant (10-15%) late incidence of pulmonary hypertension, with or without interstitial lung disease, skin calcification, telangiectasiae and gastrointestinal involvement. It was previously called CREST, an acronym (Calcinosis, Raynaud, Esophagus, Sclerodactily, Telangiectasiae). Anticentromere antibodies are detected in 70-80% of patients. Because sclerodermia can affect so many different organs, it is difficult to diagnose. Here again, diagnosis is based on clinical tests such as for example complete blood call count (CBC), serum CXCL4 level, autoantibody assays using ELISA. Nevertheless, ELISA is unable to identify proteins fragments or peptides generated by protein clivage during a proteolytic activity in an inflammation process. No method is available to detect sclerodermia at an early stage All tests available on the market to identify immune-mediated inflammatory disease are related to a late-stage disease, and there is currently no effective biochemical test to make an early diagnosis, predict the course of the disease throughout the time, or monitor response to therapy. Whilst there is currently no pharmaceutical treatment for IMIDs that can alter the course of the disease, many research programs aim to develop new drug therapies. However these programs are significantly hampered by the lack of good biochemical methods for early detection, and monitoring the disease progression.

To obtain a more accurate diagnosis, it is necessary to use proteomics and its robust statistical analysis to identify protein markers, by comparison with information stored in large genomics databases.

Proteomics uses generally mass spectrometry and a significant improvement in diagnosis is obtained when time of flight-mass spectrometry (SELDI-TOF-MS) is involved.

For example in WO 2012/104624 the surface enhanced laser desorption/ionization-time of flight-mass spectrometry (SELDI-TOF-MS), a semi-quantitative proteomic approach, was used to investigate differential expression level of proteins. High or low proteins signals are of the main interest and considered as potential biomarkers of the disease process. However, these method only provide information about increased or decreased level of newly discovered biomarkers in OA compared to controls, and present therefore a relative quantitation of these biomarkers.

The method disclosed in WO2012/104624 A2, allows relative quantitation of different biomarkers such as V65 vitronectin or C3f through their peaks intensity obtained with the SELDI-TOF-MS technique, but such a method does not allow an absolute quantification of the biomarkers.

We have now found an accurate method of diagnosing early-stage Immune-mediated inflammatory diseases. The method refers to LC-MS/MS technology and allows for absolute quantitation thanks to the development of stable-isotope based methods in which ratios of "light" and "heavy" versions of the same peptide are accurately determined and reported to the calibration curve to determine biomarkers concentrations.

We have further surprisingly found that both vitronectin and C3f biomarkers and their fragments, or fragments, variants, or degradation product thereof are present in immune-mediated disease at an early stage. Particularly vitronectin fragment, variant or degradation products that is generally found in tissue or extracellular matrix as degradation marker and therefore at a later stage of the IMID, is also acting as a detection marker.

The present invention refers to an in-vitro method of diagnosing or detection of immune-mediated inflammatory diseases that analyses simultaneously complement C3f and vitronectin fragments, or fragments, variants, or degradation products thereof that are simultaneously detected and quantify the concentration of both biomarkers, fragments, or fragments, variants or degradation product thereof by LC/MS-MS from a sample obtained from a subject.

Preferably, the method uses micro fluidic liquid chromatography coupled to a nanoelectrospray source ion trap mass spectrometry.

The subject is preferably a mammal, especially a primate.

In one embodiment the subject is a human.

The sample may be any sample obtainable from the subject, such as blood, plasma, serum, urine or synovial fluid. The sample is preferably a serum sample.

Complement C3f is a complement fragment and is well known in the art. It is a fragment released during the catabolic degradation of C3b by factor H after C3 activation. Fragments or variants of C3f are modified, especially truncated, forms of C3f or forms in which one, two, three, four or more amino acids have been removed from the C-terminal end of the peptide. The amino acid sequences of the C3f fragment is:

SSKITHRIHWESASLLR. It is a 17 amino acids fragment 1304-1320.

Vitronectin fragment is 17 amino acids fragment located at the C-terminal end product of the V65 vitronectin subunit in the heparin-binding domain. The amino acid sequence of the C-terminal V65 vitronectin fragment is:

SQRGHSRGRNQNSRRPS.

The present invention, deals therefore with a new continuous method by LC/MS-MS that combines a simultaneous and absolute quantitation of C3f ($_{1304}$SSKITHRIHWESASLLR$_{1320}$) and vitronectin ($_{381}$SQRGHSRGRNQNSRRPS$_{397}$) fragments, variants or degradation products thereof in sample such as for example in serum sample.

Combination of both quantifications is of high interest as it considerably saves analysis time. Further, particularly for OA, it covers two different processes: innate immunity/inflammation for C3f and extracellular matrix degradation for vitronectin fragment.

Preferably the method according to present invention comprises the following steps:
mixing the biological sample with an acidic aqueous solution;
loading the resulting mixture on a trapping LC column;

optionally washing the column to remove uncertain component;

eluting the column with an alcoholic mixture and obtaining an eluate;

drying the eluate;

dispersing the dried eluate in an acetonitrile aqueous solution;

loading the resulting dispersion on a reversed phase LC column and separating two eluted mobile phase A and B;

injecting by continuous flux in MS-MS, both phases A and B and quantifying V65 vitronectin fragment or fragment, variant or degradation product thereof simultaneously to quantifying complement C3f or fragment, variant or degradation product thereof.

Most preferably, the acidic aqueous solution comprises trifluoro acetic acid (TFA) at a concentration between 0.5 to 2% v; preferably 1% v Most preferably, the alcoholic mixture is methanol/water/TFA in a ratio from 90:7:3 to 90:9:1 v/v/v, preferably 90:9:1 v/v/v.

Most preferably the acetonitrile aqueous solution comprises TFA in a ratio acetonitrile/water/TFA from 3:97:0.1 to 1:99:0.1 v/v/v preferably 1:99:0.1 v/v/v By reversed phase LC column, one means for example a weak cation exchange (WCX) column The MS/MS method used in the present invention is preferably an electrospray ionization mass spectrometry (ESI) that can directly interface with liquid chromatography. Preference is given to an ion trap or a triple quadrupole mass spectrometry; most preferably a nanoelectrospray source ion trap spectrometry wherein C3f or fragment, variant or degradation product thereof are quantified at m/z 459.3, 530.7 and 646.3 and wherein V65 vitronectin fragment or fragment, variant or degradation product thereof are quantified at m/z 434.9, 445.2, 460.5, 466.2, 469.7, 480.3, 485.3.

In a preferred embodiment the method according to the invention is applied to Osteoarthritis (OA) as an IMID disorder and surprisingly identified significant concentration of vitronectin together with C3f at an early stage of OA Both protein fragments, identified as vitronectin fragment and C3f peptide, were found to be expressed at higher levels in sera of OA patients at all four K&L scores compared to HV and RA, and were related to OA severity.

In another preferred embodiment, the method of the invention is applied to systemic lupus erythematosus (SLE).

According to still another preferred embodiment, the method of the invention is also applied to Sclerodermia.

In IMIDs, such as OA, SLE, sclerodermia, C3f and V65 vitronectin fragment are detected at a concentration higher compared to the concentration detected in healthy subject and in a lower ratio for other pathologies such as RA, spondylarthropathies, UC and Crohn's disease.

The present invention will now be described in more details by way of examples with references to figures.

Figure 4A:
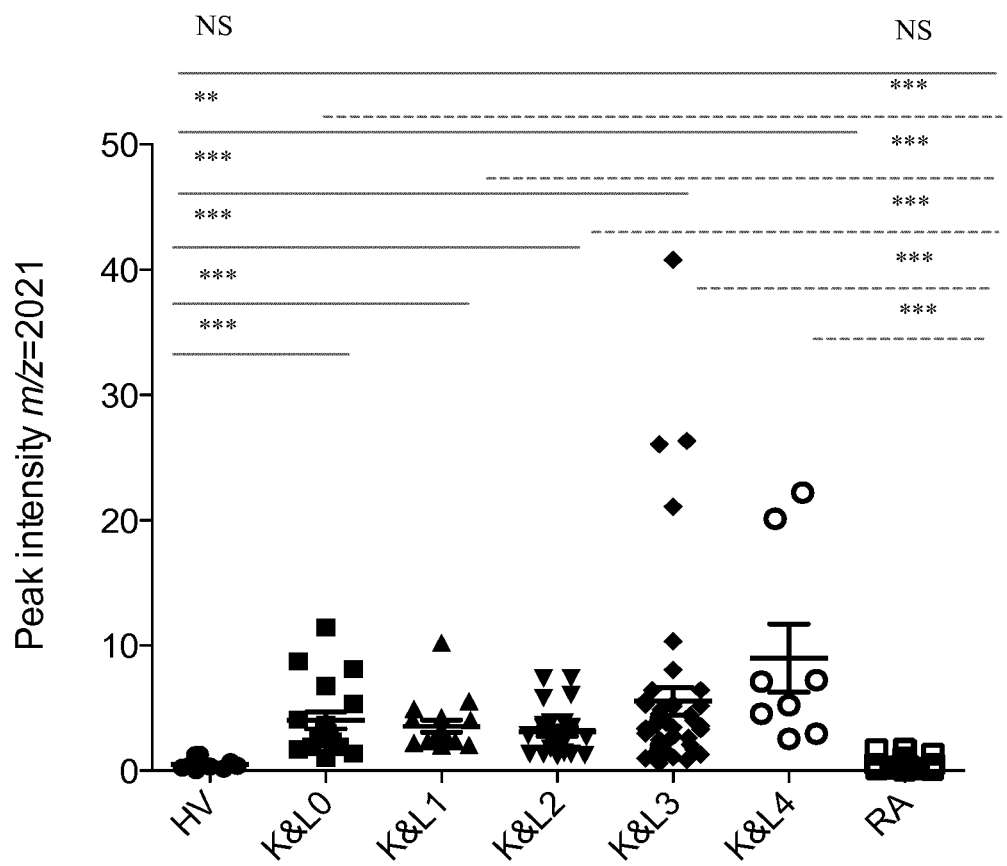
FIG. 4 illustrates a comparison between the method of the state of the art (WO2012/104264) wherein C3f and vitronectin fragments in serum samples (n=147) are detected by SELDI-TOF-MS (relative quantitation) and compared to the method according to the present invention wherein C3f and vitronectin fragments in serum samples are detected and quantify by LC-MS/MS (absolute quantitation).
Figure 4B:
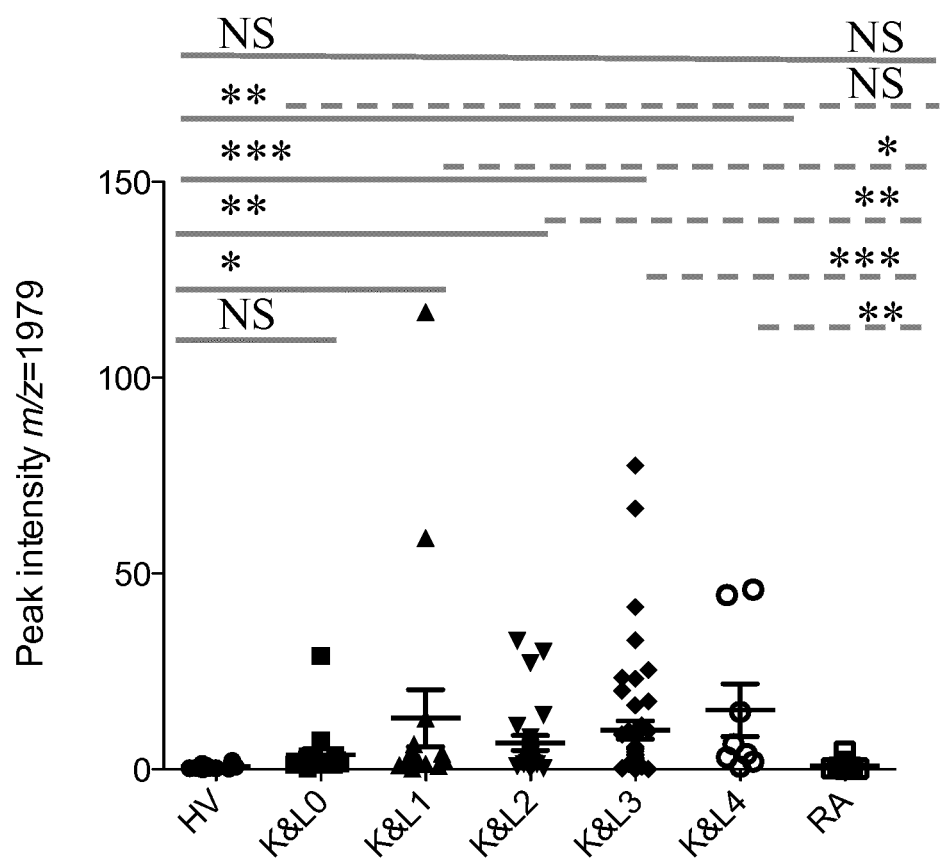

Samples were classified into 7 groups: HV (n=12), K&O (n=18), K&L1 (n=17), K&L2 (n=25), K&L3 (n=48), K&L4 (n=8) and RA (n=19). Peak intensities of C3f and vitronectin fragments obtained by SELDI-TOF-MS are illustrated in FIGS. 4A and 4B.

Figure 4C:
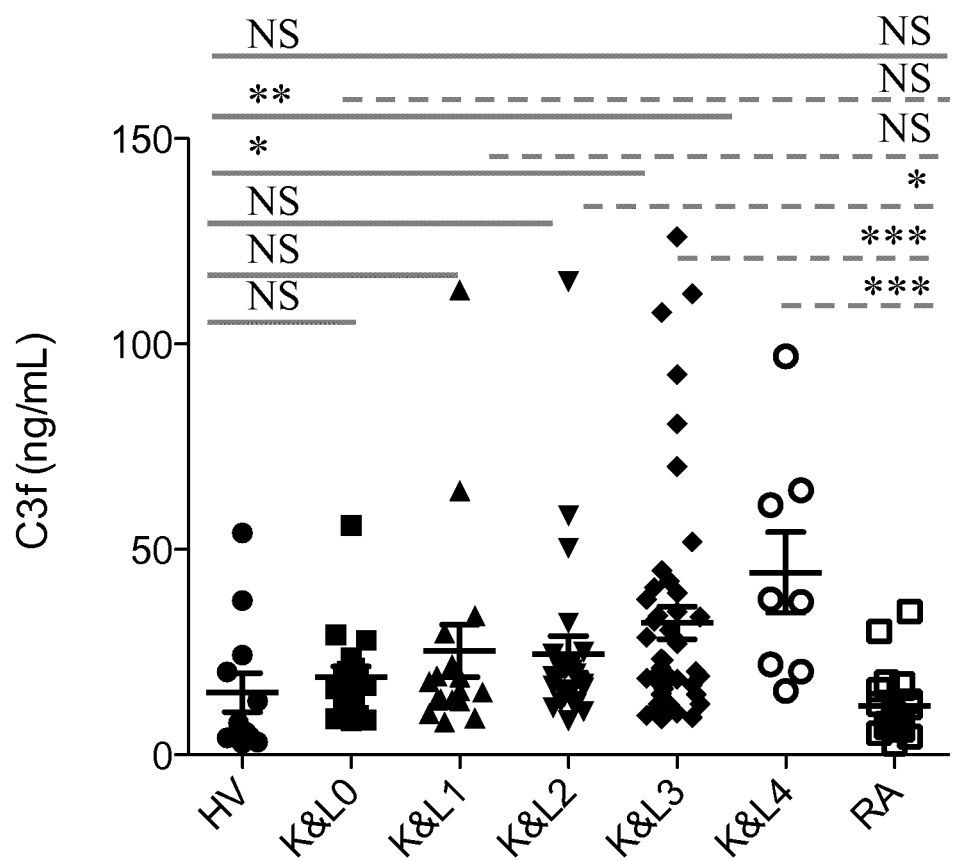
Figure 4D:
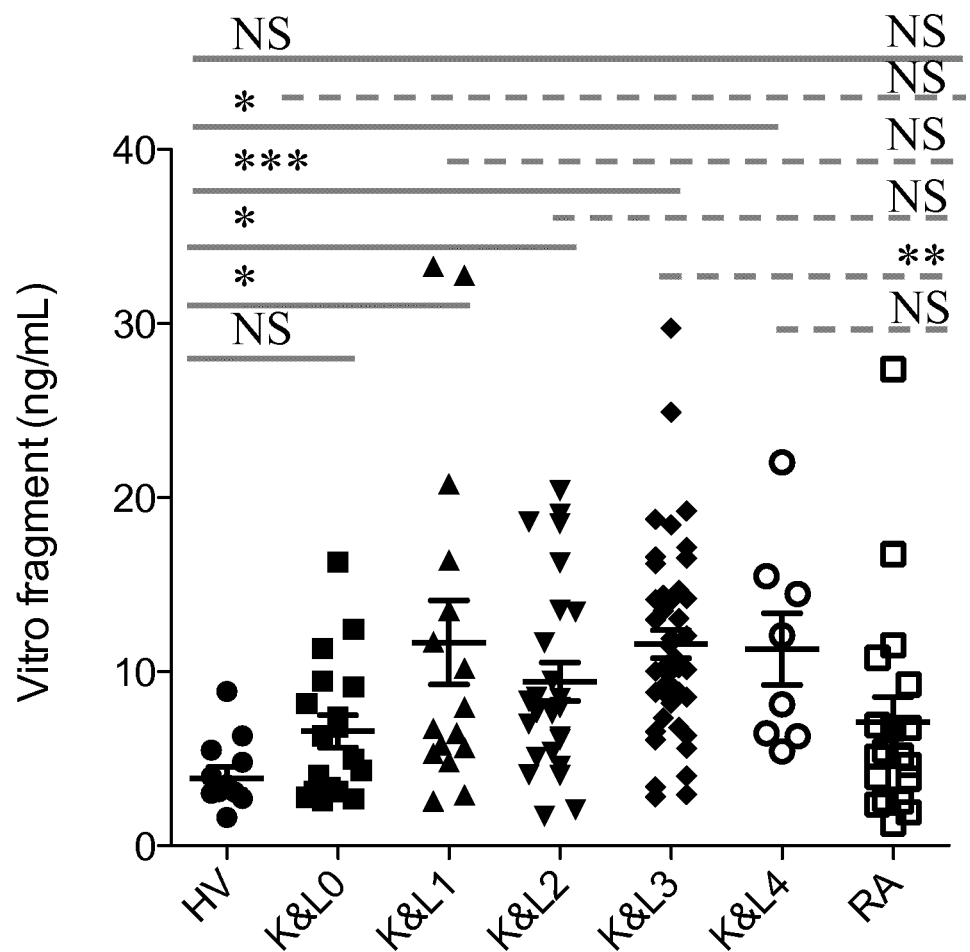

Concentrations of C3f and vitronectin fragments obtained by LC-MS/MS according to the invention are illustrated in FIGS. 4C and 4D.

Figure 4E:
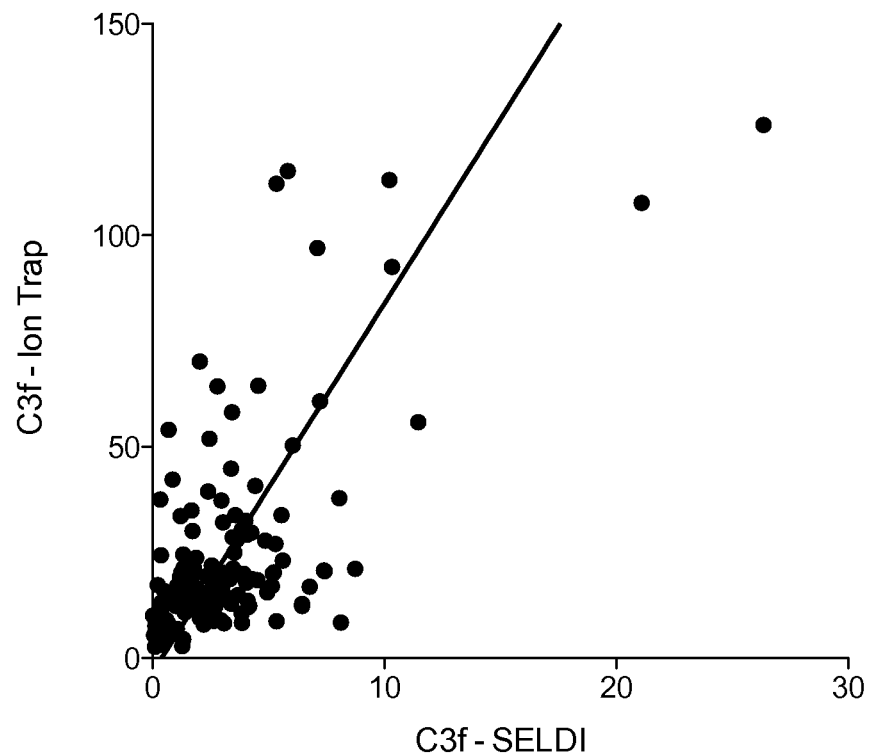
Figure 4F:
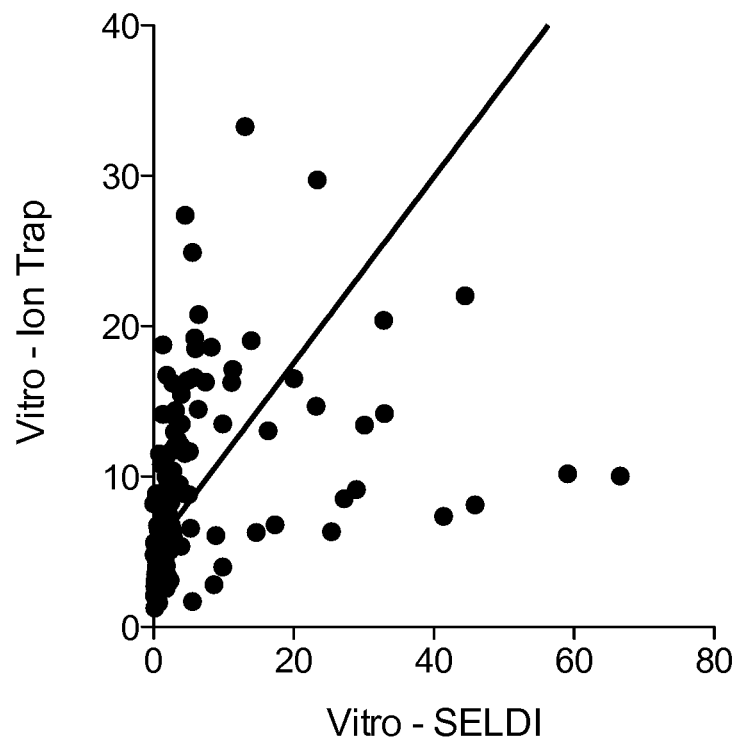

Both methods, SELDI-TOF-MS and LC-MS/MS (also called LC-chip-MS/MS), are then compared in FIGS. 4E and 4F. C3f and vitronectin peak intensities obtained by SELDI-TOF-MS are correlated to C3f and vitronectin concentrations obtained by LC-MS/MS (r=Spearman correlation). Deming regression analysis was performed.

Figure 5:
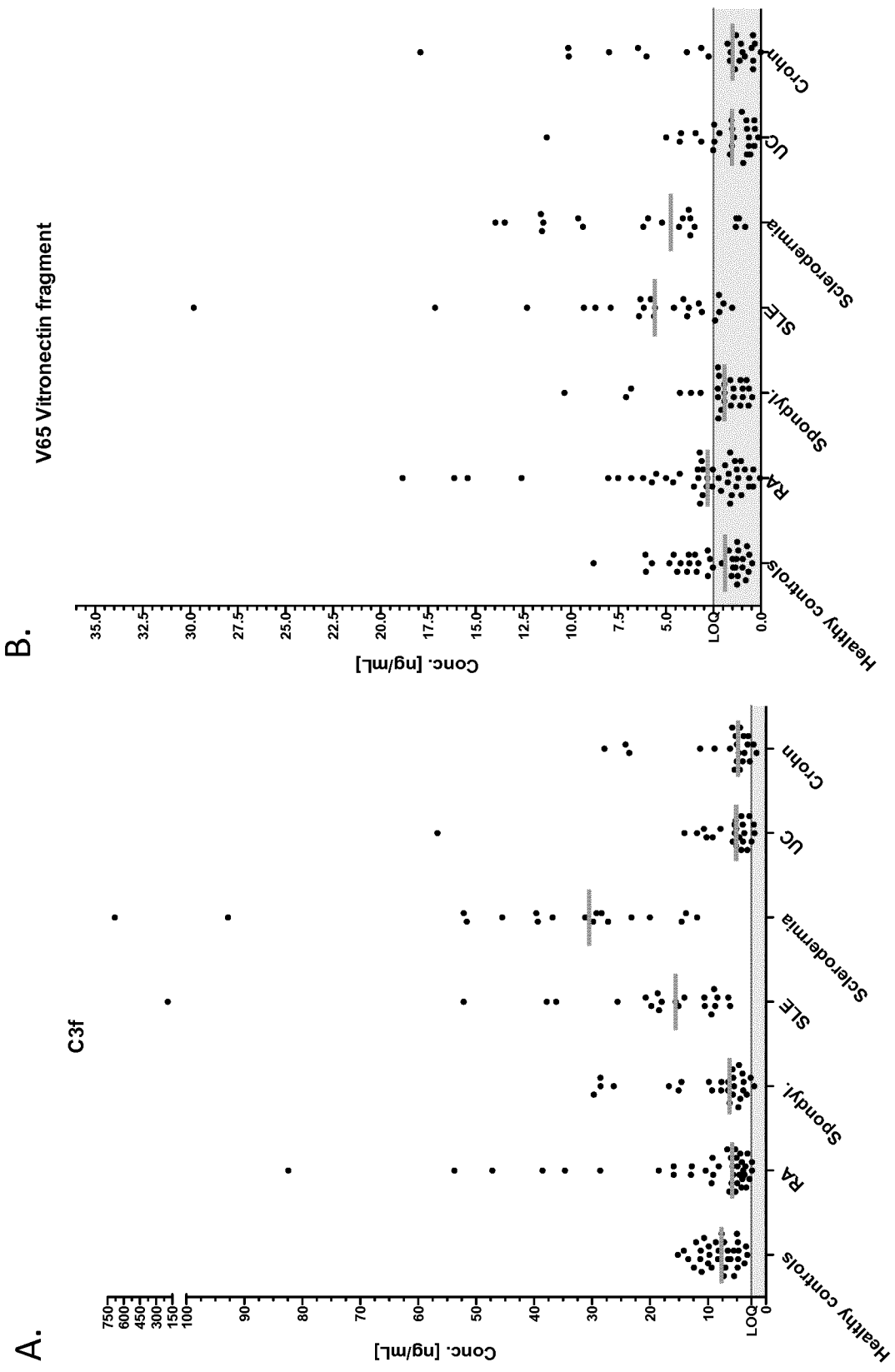

FIG. 5: Quantitation of C3f and V65 vitronectin fragments in serum samples (n=209) by LC-MS/MS according to the method of the invention. Samples were classified into 7 groups: HV (n=41), RA (n=46), ankylosing spondylitis (n=27), SLE (n=23), sclerodermia (n=20), UC (n=27) and Crohn (n=25). Concentrations of C3f and vitronectin fragments obtained by LC-MS/MS were illustrated in FIGS. 5A and 5B.

DETAILED DESCRIPTION

Definitions of Abbreviations Used in the Present Description
OA: osteoarthritis
HV: healthy volunteers
RA: rheumatoid arthritis
SLE: Systemic lupus erythematosus
UC: Ulcerative colitis
SELDI-TOF-MS: surface enhanced laser desorption/ionization-time of flight
mass spectrometry
JSN: joint space narrowing
LC: liquid chromatography
MeOH: methanol
ACN: acetonitrile
FA: formic acid
TFA: trifluoroacetic acid
$NH_4OAc$: ammonium acetate
$NH_4OH$: ammonium hydroxide
ESI: electrospray ionization source
m/z: mass-to-charge ratio
EIC: extracted ion current
NSAID: non steroidal anti-inflammatory drug
LLOQ: lower limit of quantitation
HLB: hydrophilic-lipophilic balance
MCX: mixed-mode cationic exchange PE: process efficiency
ME: matrix effect
ER: extraction recovery
EY: extraction yield Classification According to Grade of Severity The Kellgren and Lawrence (K&L) score (0-4) as reported in Annals of the rheumatic disease 1957; 16: 494-502 is used to classify biomarker expression levels detected in samples of patients with knee OA according to their grade of severity. The K&L classification is running from 1 to 4 after X-ray examination. K&L0, 1 and 2 scores represent the first stages of OA development, for which X-ray cannot detect joint narrowing space and bone sclerosis. K&L3 and 4 are further associated to the late stages of OA with marked joint space narrowing, bone sclerosis and presence of multiple osteophytes.

Early stage of diagnosis as defined in the present invention corresponds to K&L0 for OA. No corresponding K&L classification is reported for the other IMIDs.

LC/MS-MS

The method according to the invention starts with a weak cation exchange such as WCX SPE 96 well plates approach that was selected for the purification and enrichment process of both fragments. A Liquid Chromatography (LC) is then carried out for a separation of peptides fragments or fragment, variant or degradation product thereof and is continuously followed by a double MS detection of respectively the peptides and their fragments or variant or degradation products thereof. Several parameters for LC separation and for MS/MS detection were optimized to get two independent time windows for C3f and vitronectin fragments quantitation. The developed method for C3f and vitronectin fragment quantitation in sample was fully validated. After having selected the most appropriate regression model on the basis of the accuracy profiles, method selectivity, trueness, precision, accuracy and linearity were demonstrated according to a well known method with e-noval software as disclosed for example in U.S. Pat. No. 8,494,818B2.

This new absolute quantitative method according to the invention, was applied to the analysis of different IMID samples previously analyzed by SELDI-TOF-MS. IMIDs were classified according to severity. It has been surprisingly found that the new absolute method according to the invention allows to detect vitronectin fragment and complement C3f fragment in the early stage of IMID samples.

Example 1: Application of the Method According to the Invention to Osteoarthritis For example this new absolute quantitative method according to the invention, was applied to the analysis of different samples such as serum samples (n=147) previously analyzed by SELDI-TOF-MS on OA serum samples. OA samples were classified according to OA severity, which is characterized by the K&L classification from 1 to 4 after X-ray examination. OA serum samples were also compared to RA serum samples to assess the specificity of C3f and vitronectin fragments. Healthy Volunteers (HV) serum samples were also included to determine the starting concentration of C3f and vitronectin fragments in normal serum.

Similarly to the SELDI-TOF-MS analysis, we observed by LC-MS/MS that C3f and vitronectin fragments levels increased with OA severity. Compared to HV, C3f fragment showed statistically increased expression in stages of OA where Joint Space Narrowing (JSN) is definite (K&L3-4 scores) compared to HV. Compared to RA, it was already statistically increased in the earlier stage with definite osteophyte and possible JSN (K&L2 score) of OA. Further, within OA patients, C3f fragment showed statistically increased expression in the K&L3-4 scores compared to K&L1-2 scores. C3f biomarker could therefore approach the definition of a "burden of disease" biomarker assessing disease severity in individuals with OA. Compared to HV, vitronectin fragment showed statistically increased expression in most K&L scores. Vitronectin fragment biomarker could therefore approach the definition of a "diagnostic" biomarker distinguishing between individuals with and without OA.

In this comparison study, we observe that both C3f and vitronectin fragments increase with OA severity. We also observe that C3f fragment is more related to the severity of OA, whereas vitronectin fragment is more related to early OA detection.

Materials and Methods

Methods Summary:

Microfluidic liquid chromatography coupled to a nano-electrospray source ion trap mass spectrometry was used for the absolute and simultaneous quantitation of C3f and vitronectin fragments in serum. The method was first carefully optimized and then validated in serum biological matrix according to FDA guidelines. Stable isotopes for the two biomarkers of interest were used as internal standards. Microelution solid phase extraction in 96-well plate format was used to purify and concentrate C3f and vitronectin fragments. Parameters for liquid chromatophraphy and for mass spectrometry were simultaneously optimized for C3f and vitronectin fragments quantitation. Serum samples (n=147) classified in 7 groups [(healthy volunteers, OA with 5 grades of severity and rheumatoid arthritis (RA) patients] were analyzed with our new quantitative method.

Chemicals

Water, methanol (MeOH), acetonitrile (ACN) and formic acid (FA) 99% were all at LC/MS grade and were purchased from Biosolve. Trifluoroacetic acid (TFA) was obtained from Fluka. Ammonium hydroxide ($NH_4OH$) was purchased from Merck and ammonium acetate ($NH_4OAc$) 98.9% from VWR. Helium and nitrogen (Alphagaz 2) were obtained from Air Liquide. Human synthetic complement C3f fragment ($_{1304}$SSKITHRIHWESASLLR$_{1320}$), vitronectin fragment ($_{381}$SQRGHSRGRNQNSRRPS$_{397}$) and the internal standard [$^{13}C_6$, $^{15}N_2$]Lys$^3$, [$^{13}C_6$, $^{15}N_4$]Arg$^{17}$-Complement C3f, [$^{13}C_6$, $^{15}N_4$]Arg$^{3,15}$-vitronectin fragment were purchased from Eurogentec.

Instruments

Solid-phase extraction procedure was carried out by Oasis μElution weak cation exchange (WCX) 96 well plates with a vacuum manifold (Waters Inc.) for peptides extraction and enrichment. Sample evaporation was performed on a vacuum concentrator (Labconco). A 1200 series LC-system including nanoflow pump, a capillary pump, a well plate sampler and a LC/MS interface was used for chromatographic separation. ChemStation (Agilent Technologies) is a software package to control Agilent liquid chromatography system. Protonated peptides detection was performed by Ion Trap mass spectrometry combined with a nanoelectrospray ionisation source operating in positive mode (Agilent Technologies). TrapControl (Bruker Daltonik GmbH) determined the mass spectrometry detection parameters. Raw data obtained by mass spectrometry were processed using DataAnalysis and QuantAnalysis softwares (Bruker Daltonik GmbH).

Internal Standards and Calibration Standards

All peptides (labeled and unlabeled) were dissolved in a $H_2O/ACN/FA$ (80:20:0.1; v/v/v) solution to reach a concentration of 1 mg/mL, then were aliquoted and stored at −80° C. Isotopically labeled peptides ($[^{13}C_6, ^{15}N_2]Lys^3$, $[^{13}C_6, ^{15}N_4]Arg^{17}$-complement C3f and $[^{13}C_6, ^{15}N_4]Arg^{3, 15}$-vitronectin fragment) were used as internal standard for the two biomarkers of interest (complement C3f and vitronectin fragments) since they share the same physicochemical properties. Internal standard at a final concentration of 25 ng/mL and 10 ng/mL for complement C3f and vitronectin fragments, respectively, were prepared in $H_2O/TFA$ (99:1; v/v) solution. Calibration standards of complement C3f and vitronectin fragments were then diluted in $H_2O/TFA$ (99:1; v/v) solution in the range of 2.5 to 200 ng/mL at seven concentration levels (2.5, 5, 10, 20, 50, 100 and 200 ng/mL) for C3f and in the range of 2.5 to 100 ng/mL at six concentration levels (2.5, 5, 10, 20, 50 and 100 ng/mL) for vitronectin fragment.

Solid Phase Extraction Procedure

Serum samples were thawed at room temperature, vortexed and centrifuged during 5 min at 13,400 rpm. A Waters Oasis µElution WCX 96 well plate was used to purify and concentrate peptides of interest before chromatographic separation and mass spectrometry analysis. The sorbent conditioning for the OASIS-WCX was first 300 µL of MeOH followed by 300 µL of water. 100 µl of diluted human serum samples were prepared as follows: 10 µL of human serum+50 µL of $H_2O/TFA$ (99:1; v/v) solution+40 µL of internal standards (of C3f and vitronectin fragments). 100 µL of calibration standards were prepared as follows: 10 µL of calibration standards at expected concentration (of C3f and vitronectin fragments)+10 µL of serum bovine (Sigma, B9433)+40 µL of in $H_2O/TFA$ (99:1; v/v) solution+40 µL of internal standards (of C3f and vitronectin fragments). The 100 µL of diluted serum or calibration standards were then transferred in the well and drawn through the sorbent with a vacuum manifold. The plate was then washed with 200 µL $NH_4OAc$ 25 mM, pH6.8, 200 µL of $MeOH/H_2O/NH_4OH$ (50:47.5:2.5, v/v/v) followed by 200 µL of water. The extracts were eluted with 2×50 µL of $MeOH/H_2O/TFA$ (90:9:1, v/v/v). The eluates were then evaporated in a vacuum evaporator at 30° C. for 65 min, reconstituted in 100 µL $ACN/H_2O/TFA$ (1:99:0.1, v/v/v) and vortexed 15 min at room temperature.

LC-MS/MS Analysis

LC-Conditions

ProtID with a 40 nL trapping column and a 43 mm×75 µm analytical column, both packed with a Zorbax 300SB 5 µm C18 phase (Agilent Technologies) were used for chromatographic separation. The mobile phase A [$H_2O/TFA$ (100:0.1, v/v] and the mobile phase B [$ACN/H_2O/TFA$ (90:10:0.1, v/v/v] for the capillary pump and the mobile phase A [$H_2O/FA$ (100:0.1, v/v] and the mobile phase B [$ACN/H_2O/FA$ (90:10:0.1, v/v/v] for the nanopump, were degassed by ultrasonication for 15 min before use. During the analytical process, the sample was first loaded on the trapping column during an isocratic enrichment of the column by capillary pump with 1% of the mobile phase B at a flow rate of 4 µL/min. A flush volume of 1 µL of 1% mobile phase B was used to remove unretained components. Then, a gradient of elution starting at 1% of the mobile phase B and linearly ramping up to 90% of mobile phase B in 5 min was performed in backflush mode using the nanopump. Ninety % of mobile phase B was maintained for 2 min before coming back to 1%. Ten column volumes were finally used to re-equilibrate the column before the next injection. The time for one run was 14 min. Five µL of sample was injected. The injection needle was also thoroughly rinsed twice from inside and outside with a mix solution of $ACN/H_2O/TFA$ (60:40:0.1, v/v/v).

MS Detection

Optimization of MS detection parameters was performed by infusion experiments at a flow rate of 36 µL/h with 1 µg/mL of C3f and vitronectin fragment and their internal standards solutions. NanoESI source was operating in a positive mode. Ions optics were optimized using the Smart Ramp tool included in Trap-Control software in order to maximize precursor ion intensity for C3f, vitronectin fragment and their internal standards. Capillary voltage was set at 1800V and the endplate offset at 500V. Nitrogen was used as drying gas at a flow rate of 4 L/min and the source temperature was set at 325° C. $MS^2$ spectra were acquired in the mass-to-charge (m/z) ratio from 375 to 700 for C3f and in the m/z range of 350 to 600 for the vitronectin fragment.

The MS and MS/MS experimental parameters were optimized to be as sensitive and selective as possible. Reference peptides were first infused one by one in order to optimize source parameters and to select the most intense precursor ions ($[M+4H]^{4+}$ for both). Then, after fragmentation energy optimization, the most abundant fragment ions were selected for quantitation: m/z=459.3, 530.7 and 646.3 for C3f and m/z=434.9, 445.2, 460.5, 466.2, 469.7, 480.3, 485.3 for the V65 vitronectin fragment.

Total ion current chromatogram was handled to yield an extracted ion current (EIC) chromatogram that summed the intensities of the selected MS/MS ions for C3f and vitronectin fragment. EIC were smoothed using a 1×2 Gauss algorithm and subsequently integrated. Area ratios (peptide vs. labeled peptide) were considered for quantitation.

Serum Cohort—Epidemiological Data

The 116 OA patients from University of Bristol cohort were included to validate the quantitation of C3f and the V65 vitronectin fragment by LC-MS/MS analysis. The demographic, clinical and radiographic data of these patients were previously published in Annals of the rheumatic diseases 2011. None of the OA patients was on intra-articular steroids or any potential disease-modifying drugs, the majority was on analgesics or non-steroidal anti-inflammatory drugs (NSAIDs) that are unlikely to affect serum or synovial fluid levels of investigated markers. Nineteen RA patients fulfilling the 1987 American College of Rheumatology criteria (as described in Journal of Chromatography A 2013; 1314:199-207) and 12 healthy individuals referred to as healthy volunteers (HV) were included in the study as control subjects.

Statistics

The e.noval software (Arlenda, Liège, Belgium) was used to compute trueness, precision, accuracy for all concentrations of calibration standards, as well as lower limit of quantitation (LLOQ). It was also used to choose the most appropriate regression model.

Peak intensities (by SELDI-TOF-MS) and concentrations (by LC-MS/MS) of C3f and vitronectin fragments were compared in all groups of OA to HV and RA groups by the non-parametric Kruskal-Wallis test with a post-hoc test of Dunn's. K&L1-2 values were compared to K&L3-4 values by the non-parametric Mann-Whitney U test. P-values were statistically significant at $P<0.05$.

Correlation coefficients were calculated by the non-parametric Spearman analysis to correlate SELDI-TOF-MS data to LC-MS/MS data. Deming regression was used for regression analysis.

Results
Results Summary:

A weighted $1/x^2$ quadratic regression for C3f and a weighted $1/x$ quadratic regression for vitronectin peptide were selected for calibration curves. Trueness (with a relative bias <10%), precision (repeatability and intermediate precision <15%) and accuracy (risk <15%) of the method were successfully demonstrated. The linearity of results was validated in the dosing range of 2.5-200 ng/mL for C3f and 2.5-100 ng/mL for vitronectin fragment.

Optimization of MS/MS Detection

Figure 1A:
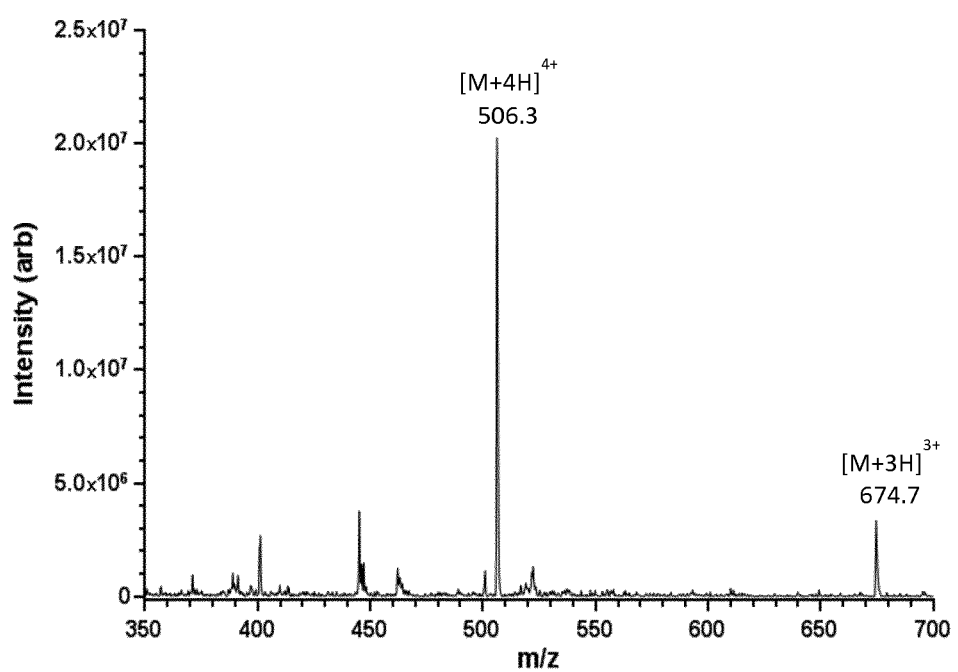
FIG. 1: (A-B) MS spectrum of C3f (aa: 1304-1320) and vitronectin (aa: 381-397) synthetic peptides and (C-D) MS/MS spectrum of their respective precursor ions ([M+4H]$^{4+}$ at m/z 506.3 and at m/z 496.0. (E-F) MS spectrum of the unlabeled and labeled peptides of C3f and vitronectin synthetic peptides. aa=amino acids FIG. 2: A. Optimal percentage of acetonitrile in the dissolution solution of lyophilized samples for both C3f and vitronectin peptides. B and C. Optimal percentage of acetonitrile for the sample loading by the capillary pump for the C3f and vitronectine peptides.
Figure 1B:
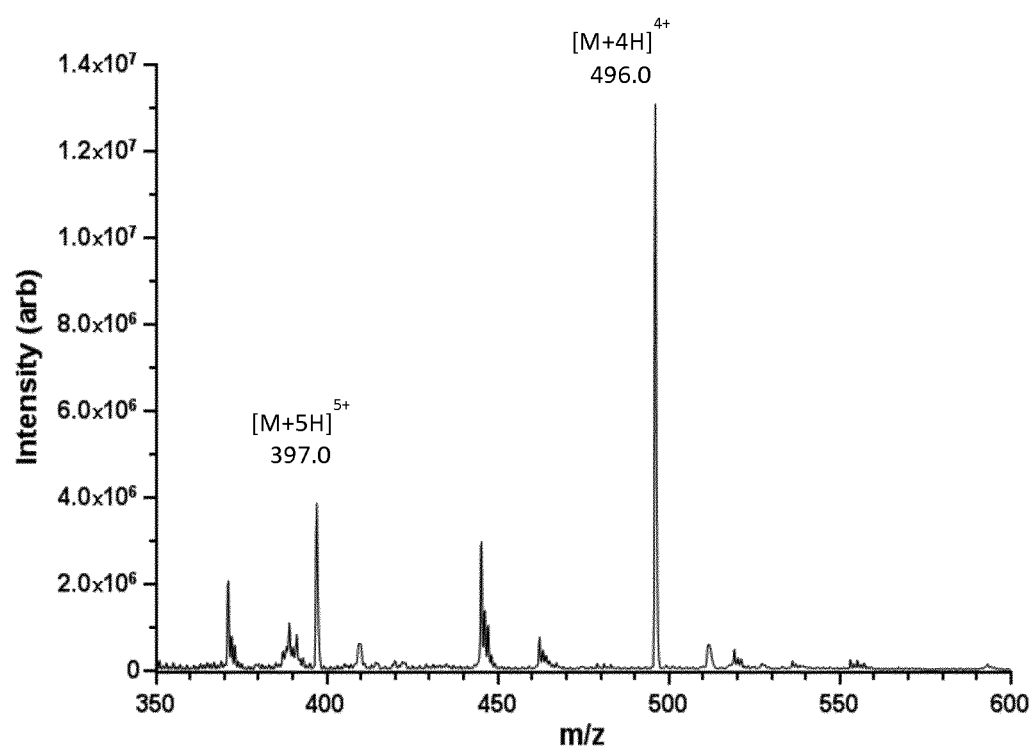
Figure 1C:
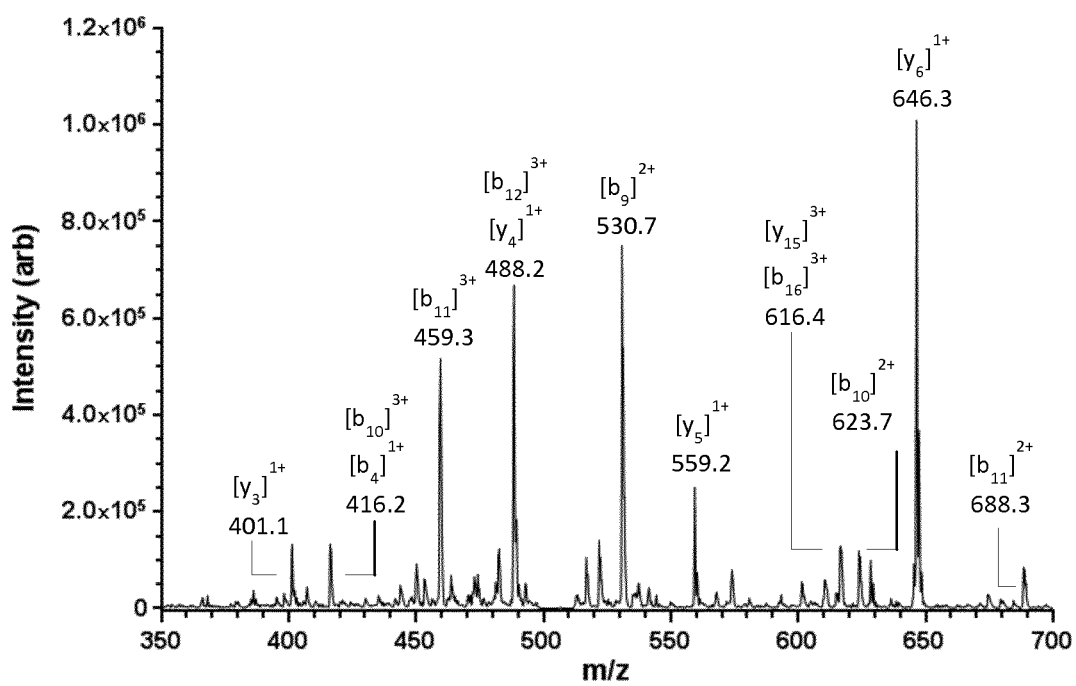
Figure 1C:
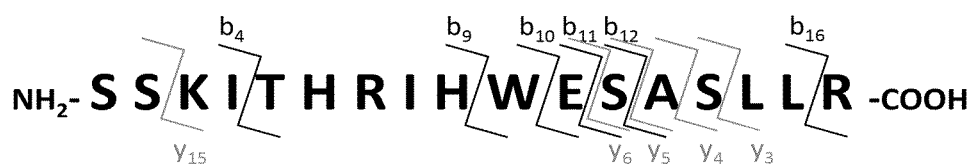
Figure 1D:
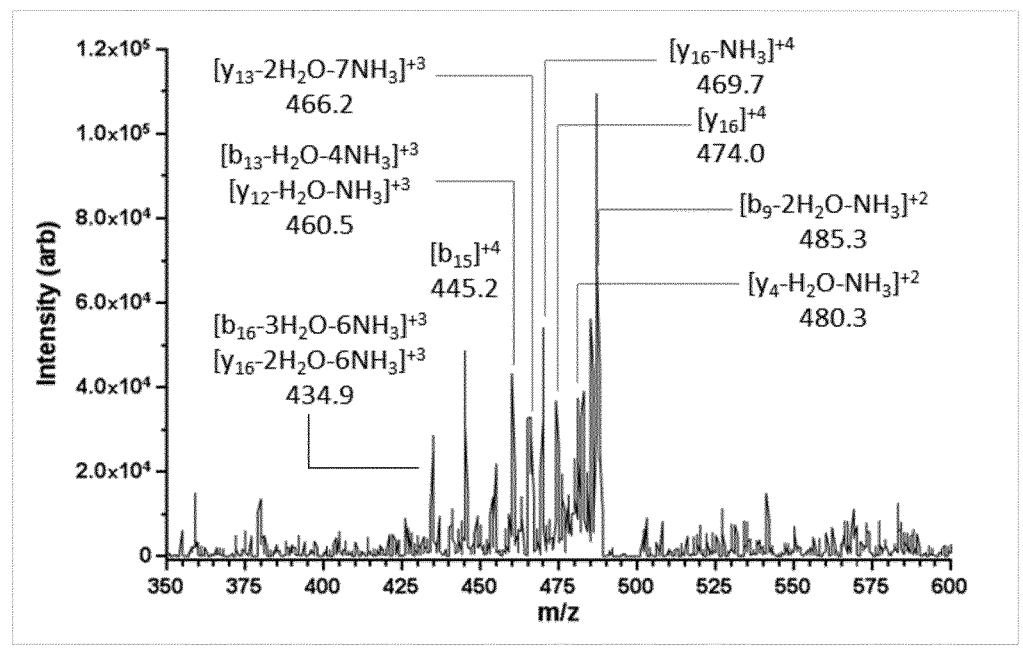
Figure 1D:

Synthetic peptides for the C3f ($_{1304}$SSKITHRIHWE-SASLLR$_{1320}$) and vitronectin ($_{381}$SQRGHSRGRNQN-SRRPS$_{397}$) fragments were first infused at a concentration of 1 μg/mL in 0.1% of TFA and analyzed in full scan mode into the ion trap in the range of m/z 200-1500. Voltages were optimized to detect the highest relative intensity using the Smart Ram tool. [M+4H]$^{4+}$ at m/z 506.3 and at m/z 496.0 were the most abundant ions observed for C3f and vitronectin synthetic peptides (FIGS. 1A and 1B) and were selected for MS/MS analysis. Fragmentation amplitudes at 0.95V and 1.1V were applied to the precursor ion of the C3f and vitronectin peptides, respectively, to generate multiply charged ions as observed in MS/MS spectra in FIGS. 1C and 1D. For quantitation, 3 fragment ions (m/z=459.3, 530.7 and 646.3) for C3f and 7 fragment ions (m/z=434.9, 445.2, 460.5, 466.2, 469.7, 480.3 and 485.3) for the V65 vitronectin fragment were selected.

Figure 1E:
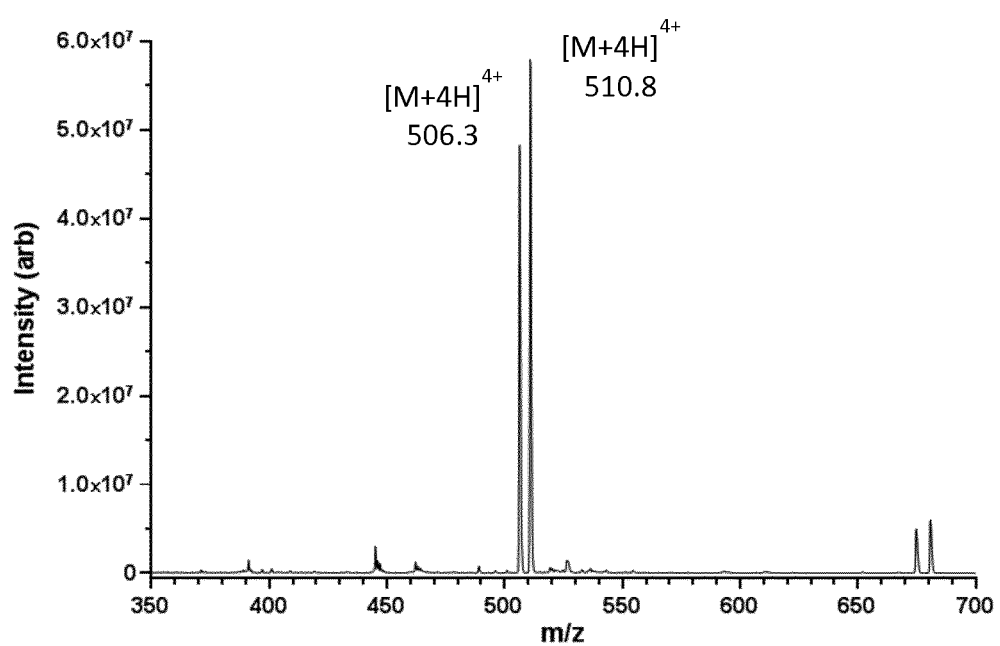
Figure 1F:
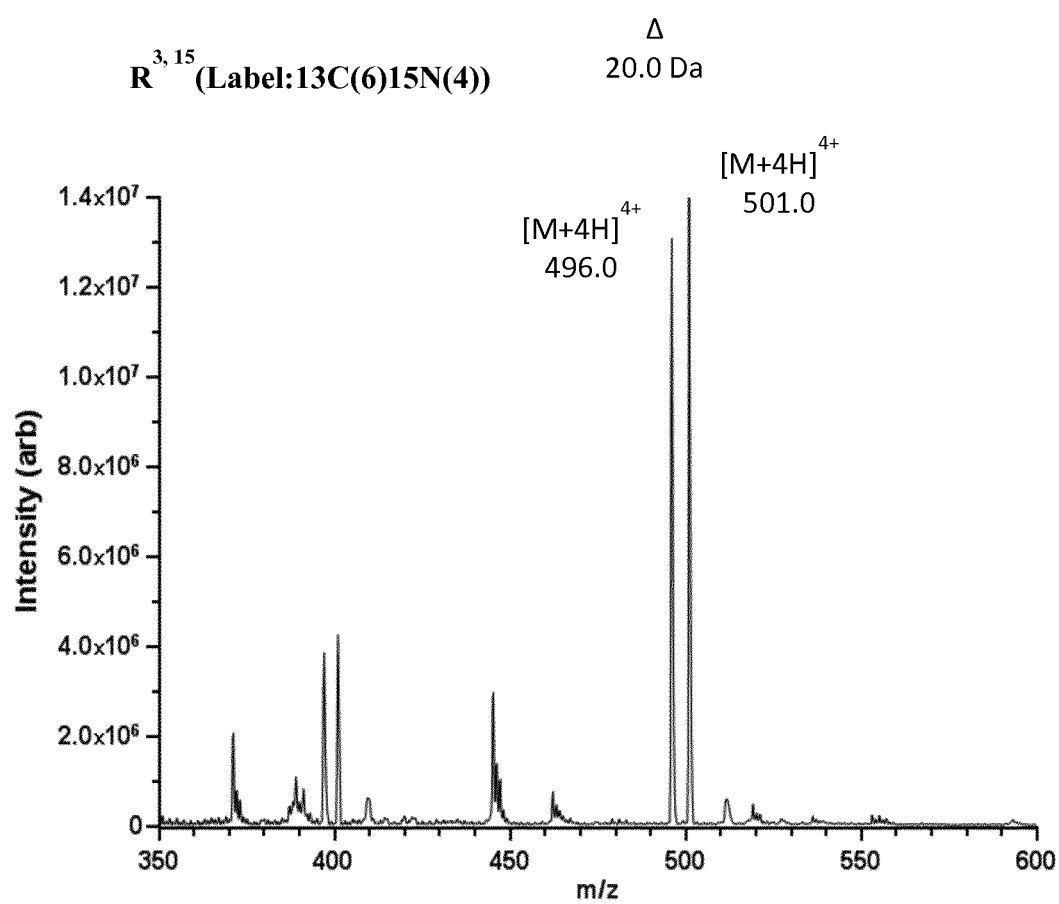

Labeled peptides were synthesized accordingly: [$^{13}C_6$, $^{15}N_2$]Lys$^3$, [$^{13}C_6$, $^{15}N_4$]Arg$^{17}$-Complement C3f and[$^{13}C_6$, $^{15}N_4$]Arg$^{3,15}$-vitronectin fragment. Both unlabeled and labeled peptides were simultaneously infused for the C3f and for the vitronectin fragment. Two precursor ions, [M+4H]$^{4+}$ at m/z 506.3 and [M+4H]$^{4+}$ at m/z 510.8, were distinctly observed for the unlabeled and labeled C3f peptides (FIG. 1E). Similarly, unlabeled ([M+4H]$^{4+}$ at m/z 496.0) and labeled ([M+4H]$^{4+}$ at m/z 501.0) peptides of the vitronectin fragment are represented in FIG. 1F.

LC Method Development

Figure 2:
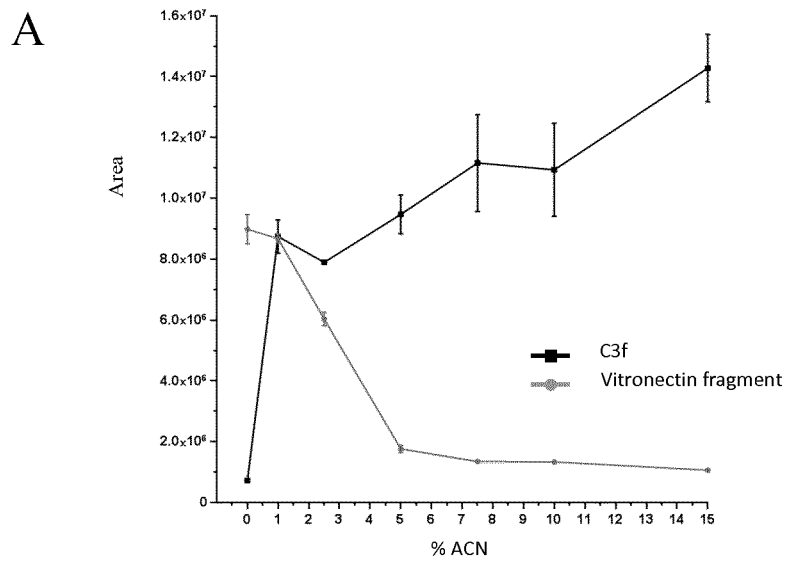
Figure 2:
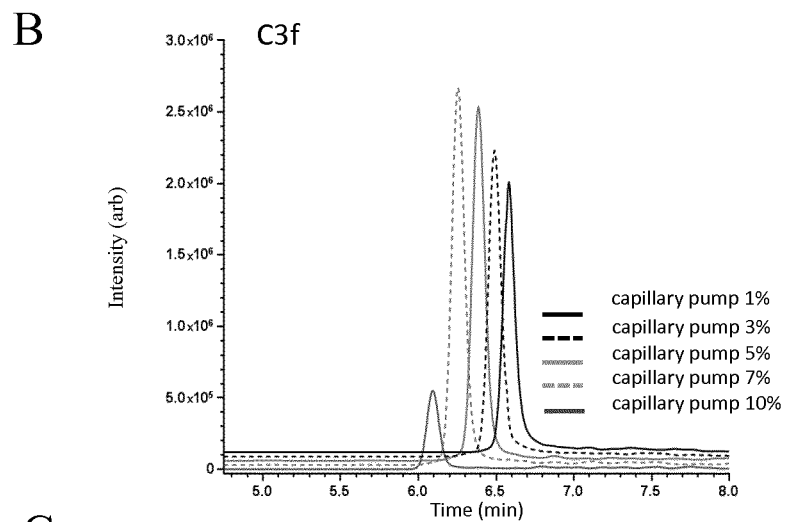
Figure 2:
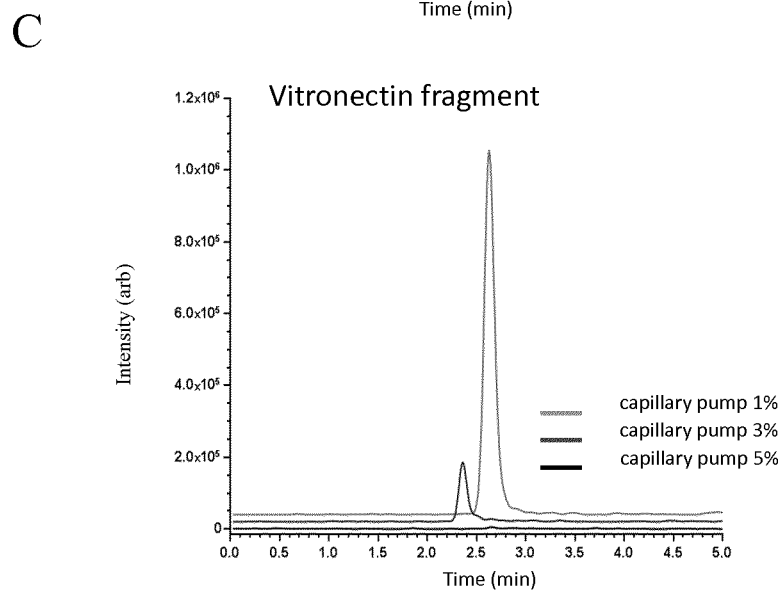
Figure 2A:
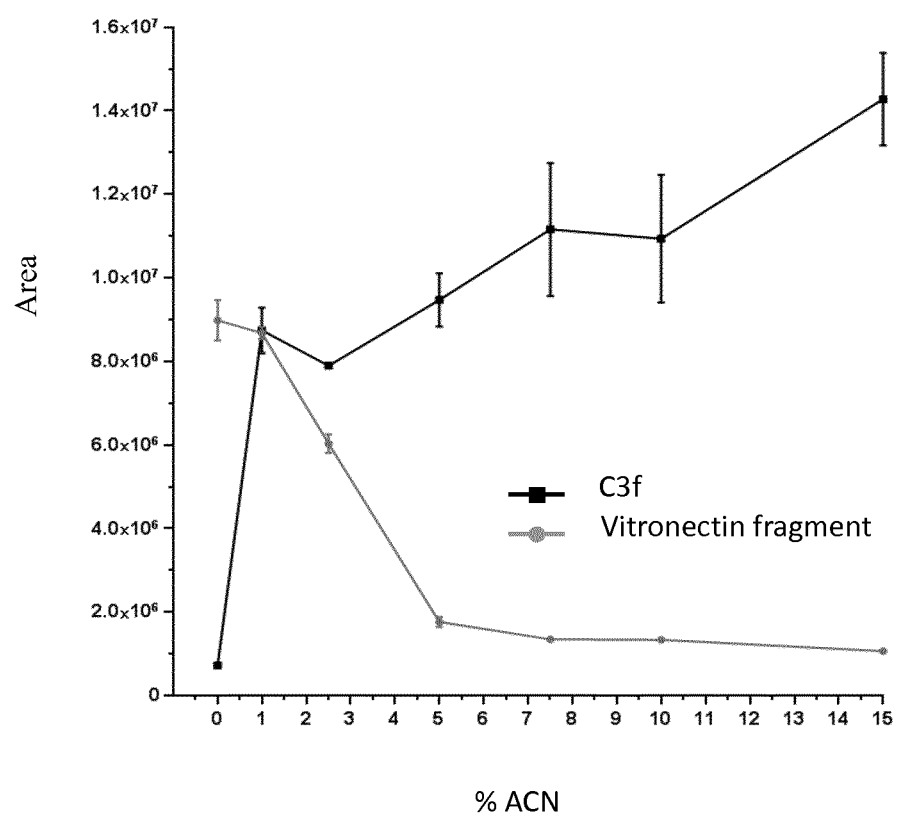
Figure 2B:
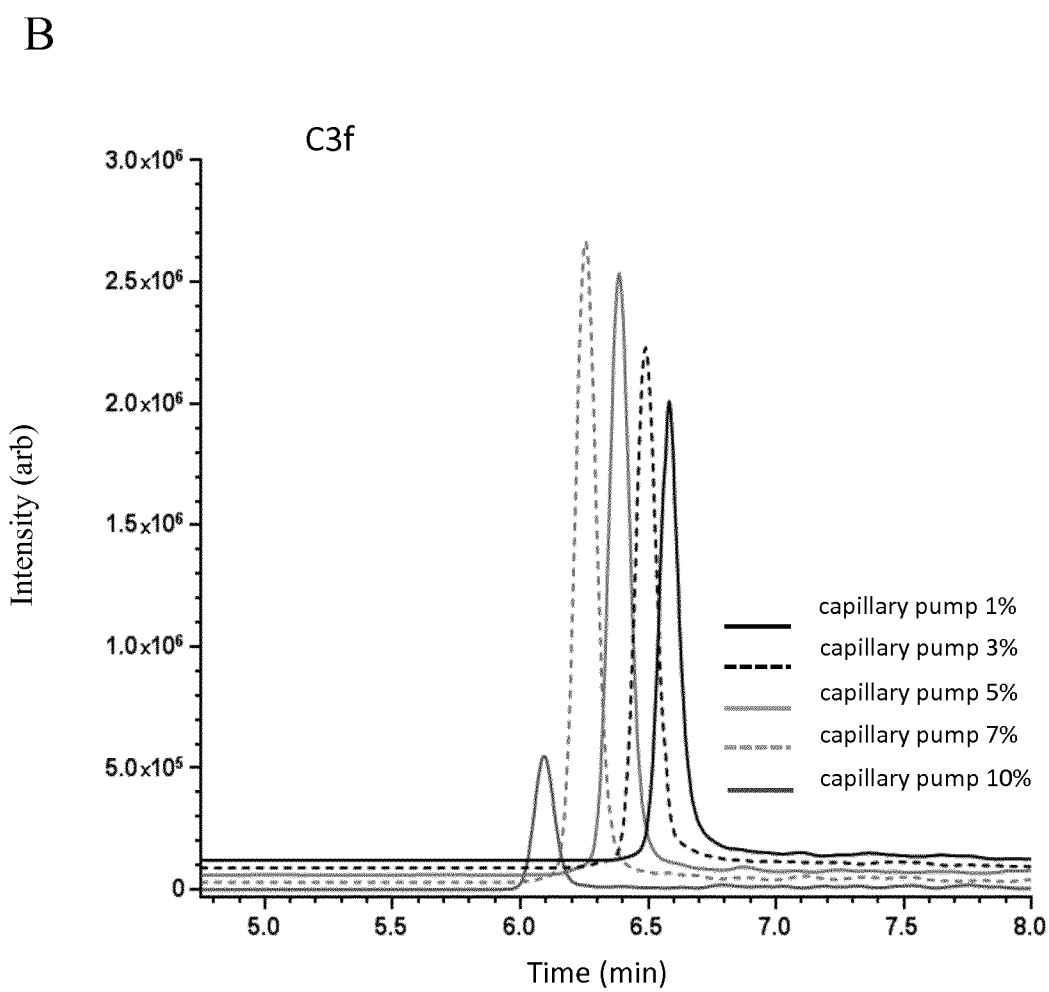
Figure 2C:
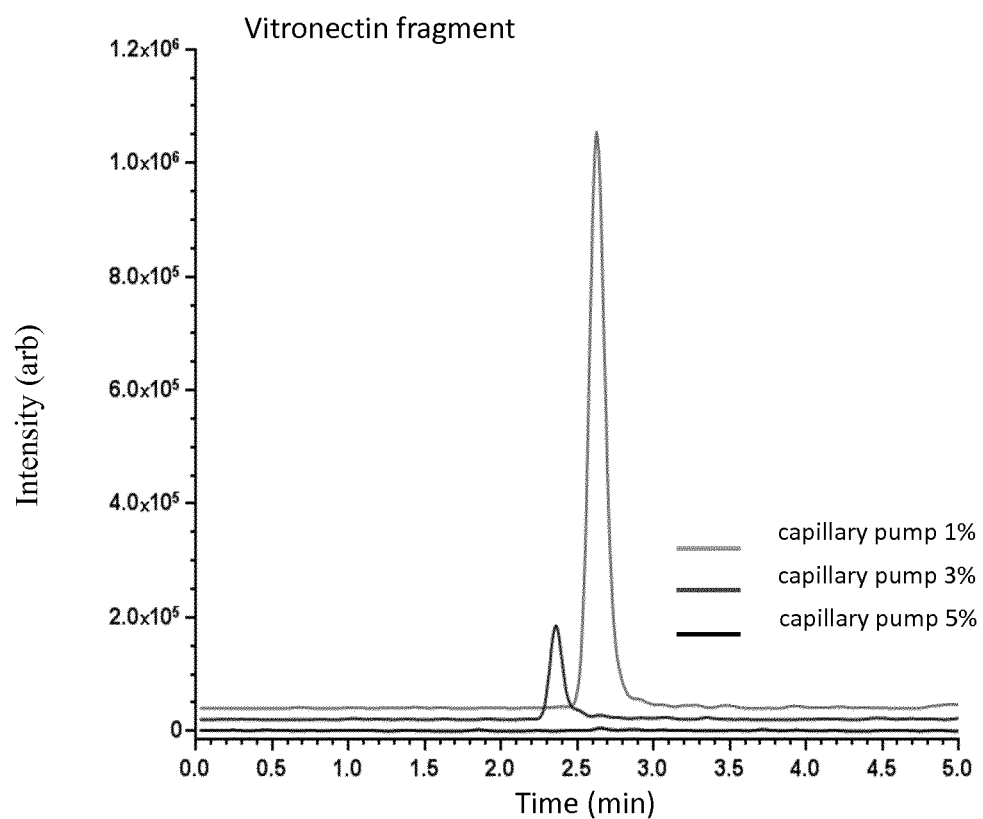

In this work, the method was developed for the simultaneous detection of C3f and vitronectin fragments in one single analysis of serum by LC-MS/MS method. All experimental conditions (mobile phases and dissolution medium composition) were optimized to reach the highest peak intensity in MS for both peptides. Synthetic peptides were diluted in a solution containing 0.1% of TFA (any retention being observed with 0.1% of formic acid for the vitronectin fragment). The dissolution solution also contained 1% ACN as the peak intensity rapidly decreased at higher percentage of ACN for the vitronectin fragment (FIG. 2A). The percentage of ACN was also optimized during the sample loading by the capillary pump and fixed at 1% in the mobile phase B as observed in FIGS. 2B and 2C. The chromatographic gradient was optimized according to previous studies reported in Journal of chromatography A 2011; 1218: 9046-54 or Journal of chromatography A 2013; 1314:199-207. Retention times of vitronectin and C3f fragments were observed at 3.5 min. (0.6% RSD) and 6.0 min. (0.1% RSD), respectively, which is sufficiently spaced to handle a time window for each peptide during MS detection and MS/MS analysis.

Solid Phase Extraction

Several Oasis μElution well plates such as WCX, HLB and MCX were tested for the purification and enrichment of C3f and vitronectin peptides before chromatographic separation and mass spectrometry analysis. Oasis WCX was the most efficient in term of recovery for both peptides. Extraction conditions were optimized and summarized in the Materials and Methods section.

Validation of the Method in Biological Fluid

Validation of this new method was then implemented on serum, the selected biological fluid.

Bovine serum was first tested to confirm that any detection of C3f and vitronectin fragment was observed by our new method. Calibration curves were then set up by preparing calibration standards of C3f and vitronectin fragments in bovine serum as described in the solid phase extraction procedure of the Materials and Methods section. Each solution was submitted to the entire process including the extraction phase in Oasis μElution WCX well plates, nano-LC retention process and injection in the nano-LC-MS/MS for analysis. For each calibration curve, all calibration standards were processed in duplicates during three days. A weighted $1/x^2$ quadratic regression for the C3f and a weighted $1/x$ quadratic regression for the vitronectin peptide were selected showing the highest accuracy and trueness index and the widest dosing range (Table 1). As summarized in Table 2, trueness (with a relative bias <10%), precision (repeatability and intermediate precision <15%) and accuracy [(risk <15%, except for the 2.5 ng/mL calibration standard of vitronectin (17,11%)] of the method were demonstrated for all concentrations of calibration standards, as well as at the lower limit of quantitation (LLOQ=2.5 ng/mL). The linearity of the results for C3f and vitronectin fragment quantitation was validated in the dosing range of 2.5-200 ng/mL for C3f and 2.5-100 ng/mL for vitronectin. The reproducibility for the retention time of the LC-chip system was also very good: 3.5 min (0.6% RSD) for the V65 vitronectin fragment and 6.0 min (0.1% RSD) for the C3f.

Figure 3:
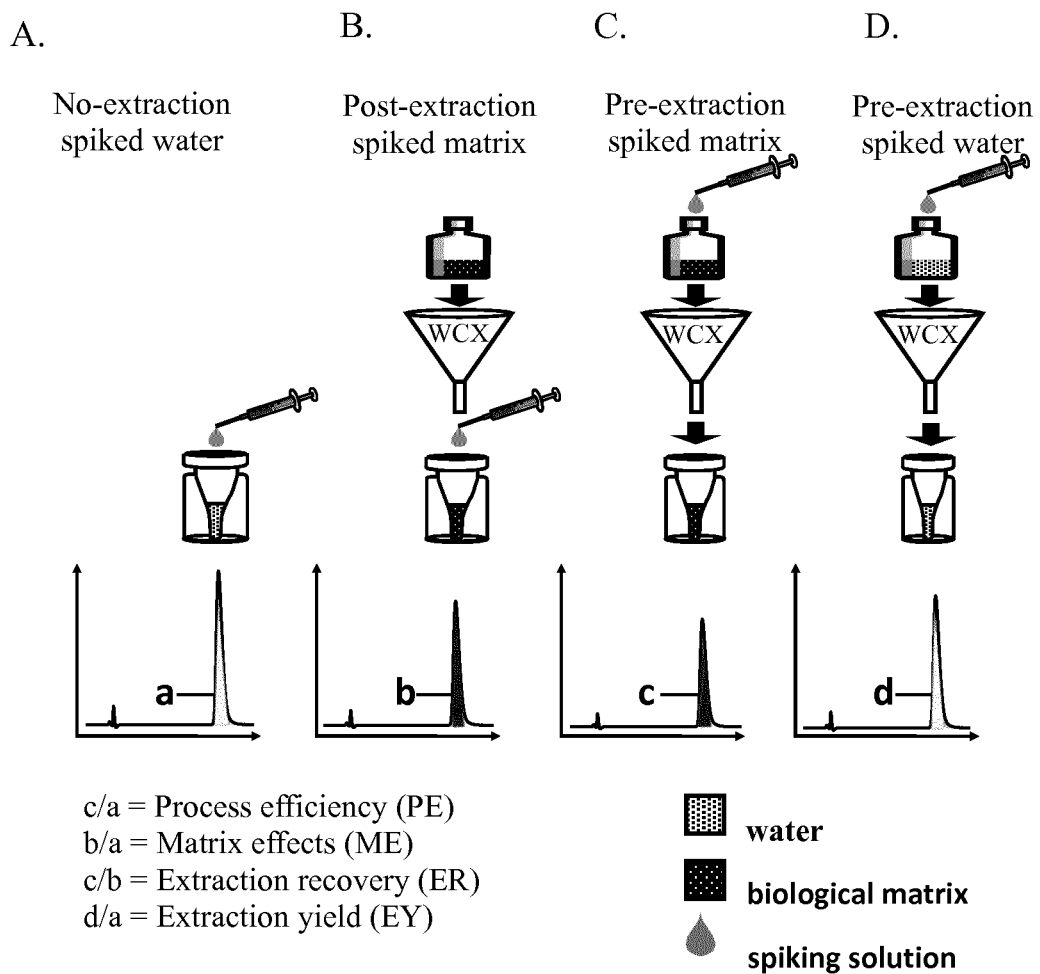
FIG. 3: Assessment of the biological matrix effect on our quantitative method according to the following parameters: process efficiency (PE), matrix effect (ME), extraction recovery (ER) and extraction yield (EY): A. represents the peak area of the standard in neat solution, B. is the peak area of the standard spiked into serum after WCX extraction, C. is the peak area of standards spiked in serum before WCX extraction and D. is the peak area of standards spiked in neat solution before WCX extraction.

The assessment of the biological matrix effect in our quantitative bio-analytical assay was also performed according to the following references J. of chromatography A 2010; 1217:3929-37 or Analytical chemistry 2003; 75: 3019-30 and Clinical biochemistry 2005; 38:328-34. Process efficiency (PE), matrix effect (ME), extraction recovery (ER) and extraction yield (EY) were summarized in FIG. 3 and demonstrated that the signal obtained for C3f (mainly) and for vitronectin (in less extent) is enhanced in the presence of serum compared to aqueous conditions.

Quantitation in Biological Sample

For quantitation, 3 fragment ions (m/z=459.3, 530.7 and 646.3) for C3f and 7 fragment ions (m/z=434.9, 445.2, 460.5, 466.2, 469.7, 480.3 and 485.3) for the V65 vitronectin fragment were selected. Both unlabeled and labeled peptides were simultaneously injected for the C3f and for the V65 vitronectin fragment. Chromatogram area ratios (peptide vs. labeled peptide) were considered for all biological samples as well as for the calibration curve. C3f and vitronectin quantitation was performed by LC-MS/MS on serum samples (n=147) provided from the previous cohort used for the SELDI-TOF-MS validation study. These samples were classified into 7 groups: HV (n=12), K&O (n=18), K&L1 (n=17), K&L2 (n=25), K&L3 (n=48), K&L4 (n=8) and RA (n=19). Peak intensities of C3f and vitronectin fragments obtained by SELDI-TOF-MS, were illustrated for all serum samples (n=147) in FIGS. 4A and 4B, respectively. Concentrations of C3f and vitronectin fragments obtained by LC-MS/MS, were illustrated for all serum samples (n=147) in FIGS. 4C and 4D, respectively. For C3f fragment, the mean concentration is 15.1 ng/mL for HV, 18.9 ng/mL for K&L0, 25.3 ng/mL for K&L1, 24.5 ng/mL for K&L2, 32.1 ng/mL for K&L3, 44.4 ng/mL for K&L4 and 11.9 ng/mL for RA. For the vitronectin fragment, the median concentration is 3.9 ng/mL for NC, 6.6 ng/mL for K&L0, 11.7 ng/mL for K&L1, 9.4 ng/mL for K&L2, 11.6 ng/mL for K&L3, 11.3 ng/mL for K&L4 and 7.1 ng/mL for RA. By SELDI-TOF-MS, C3f and vitronectin fragments levels were statistically increased in most groups of OA (except K&L0 for vitronectin fragment) compared to HV (FIGS. 4A and 4B, plain line). By LC-MS/MS, significant increased of concentrations were obtained for the vitronectin fragments at all stages including early stage (FIG. 4D) whereas C3f concentration is higher in the late stages of OA, K&L3-4 (FIG. 4C, plain line) compared to HV. Compared to RA, all groups of OA showed by SELDI-TOF-MS a statistically increased level of C3f and vitronectin fragments, except K&L0 for the vitronectin fragment (FIGS. 4A and 4B, dotted line). By LC-MS/MS, C3f mean concentration was 30 ng/ml in K&L2-3-4 and higher compared to RA (12 ng/ml) (FIG. 4C, dotted line) whereas vitronectin fragment concentration was about 11.6 ng/ml only for K&L3 compared to RA (7.1 ng/mL) (FIG. 4D, dotted line). Lastly, within OA patients, C3f fragment showed statistically increased expression in the K&L3-4 scores compared to those belonging to the K&L1-2 scores (P-value=0.032), whereas no difference were observed for the vitronectin fragment (P-value=0.054).

Both methods, SELDI-TOF-MS and LC-MS/MS, were then compared in FIGS. 4E and 4F. C3f and vitronectin peak intensities obtained by SELDI-TOF-MS were correlated to C3f and vitronectin concentrations obtained by LC-MS/MS. Correlation coefficients of 0.53 ($P<0.0001$) and 0.64 ($P<0.0001$) were obtained for C3f and vitronectin fragments, respectively.

Discussion for Osteoarthritis

We have developed a new method by LC-MS/MS that combines a simultaneous quantitation of C3f ($_{1304}$SSKITHRIHWESASLLR$_{1320}$) and vitronectin ($_{381}$SQRGHSRGRNQNSRRPS$_{397}$) fragments in serum sample. Combination of both quantifications is of high interest as it considerably decreases analysis time. Further, it allows to cover two different processes in OA: innate immunity/inflammation for C3f and extracellular matrix degradation for vitronectin fragment. WCX SPE 96 well plates approach was selected for the purification and enrichment process of both fragments. Several parameters for LC separation and for MS/MS-MS detection were optimized to get two independent time windows for C3f and vitronectin fragments quantitation. The developed method for C3f and vitronectin fragment quantitation in serum was fully validated. After having selected the most appropriate regression model on the basis of the accuracy profiles, method selectivity, trueness, precision, accuracy and linearity were demonstrated according to FDA guidelines.

This new absolute quantitative method was applied to the analysis of serum samples (n=147) previously analyzed by SELDI-TOF-MS. OA serum samples were classified according to OA severity, which is characterized by the K&L classification from 1 to 4 after X-ray examination. K&L0, 1 and 2 scores represent the first stages of OA development, for which X-ray cannot detect joint narrowing space and bone sclerosis. K&L3 and 4 are further associated to the late stages of OA with marked joint space narrowing, bone sclerosis and presence of multiple osteophytes. OA serum samples were also compared to RA serum samples to assess the specificity of C3f and vitronectin fragments. HV serum samples were also included to determine the starting concentration of C3f and vitronectin fragments in normal serum.

We observed by LC-MS/MS that C3f and vitronectin fragments levels increased with OA severity. Compared to HV, C3f fragment showed statistically increased expression in stages of OA where JSN is definite (K&L3-4 scores) compared to HV. Compared to RA, it was already statistically increased in the earlier stage with definite osteophyte and possible JSN (K&L2 score) of OA. Further, within OA patients, C3f fragment showed statistically increased expression in the K&L3-4 scores compared to K&L1-2 scores. C3f biomarker could therefore approach the definition of a "burden of disease" biomarker assessing disease severity in individuals with OA. Compared to HV, vitronectin fragment showed statistically increased expression in all K&L scores, except for K&L0, but was only statistically increased in K&L3 score compared to RA. Vitronectin fragment biomarker could therefore approach the definition of a "diagnostic" biomarker distinguishing between individuals with and without OA.

With this new absolute quantitative method, we observe that both C3f and vitronectin fragments increase with OA severity. We also observe that C3f fragment is more related to the severity of OA, whereas vitronectin fragment is more related to early OA detection.

Example 2: Application of the Method According to the Invention to Systemic Lupus Erythematosus and Sclerodermia The same experimental conditions were applied to the analysis of samples such as serum samples provided from rheumatoid arthritis (RA, n=46), spondylarthropathies (n=27), systemic lupus erythematosus (SLE, n=23), sclerodermia (n=20), ulcerative colitis (UC, n=27) and Crohn's patients (n=24). Healthy volunteers (n=41) samples were also included to determine the starting concentration of C3f and vitronectin fragments in serum samples.

We observe that median range of concentration for C3f and V65 vitronectin fragment is increased compared to healthy controls but also compared to other pathologies such as RA, spondylarthropathies, UC and Crohn's disease. C3f and V65 vitronectin fragment are present in all IMIDs tested. (FIGS. 5A and B).

Conclusions: Experimental Conditions to Carry Out the Method According to the Invention In the Solid-Phase Extraction Procedure (SPE)

The method according to the invention starts with a weak cation exchange such as WCX SPE 96 well plates approach that was selected for the purification and enrichment process of both fragments.

| Experimental Conditions SPE on WCX | Sequence |
|---|---|
| Conditioning | 300 µL MeOH |
| Equilibration | 300 µL H$_2$O |
| Loading | 100 µL 10 µL of human serum + 50 µL of H$_2$O/TFA (99:1; v/v) solution + 40 µL of internal standards. |
| Wash 1 | 200 µL NH4OAc 25 mM pH 6.8 |
| Wash 2 | 200 µL MeOH/H$_2$O/NH$_4$OH (50:47.5:2.5) (v/v/v) |
| Wash 3 | 200 µL H$_2$O 100% |
| Elution | 2 × 50 µL MeOH/H$_2$O/TFA (90:9:1) (v/v) |
| Vacuum evaporator | 65 min à 30° C. |
| Resuspention | 100 µl ACN/H$_2$O/TFA (1:99:0.1, v/v/v) Vortexed 15 min at room temperature |

In the Liquid Chromatography Separation

The method according to the invention include a liquid chromatography separation step with a hydrophobic column such as C18 approach that was selected for the separation of both fragments.

For the capillary pump: the mobile phase A [H2O/TFA (100:0.1, v/v] and the mobile phase B [ACN/H2O/TFA (90:10:0.1, v/v/v].

For the nanopump: the mobile phase A [H2O/FA (100:0.1, v/v] and the mobile phase B [ACN/H2O/FA (90:10:0.1, v/v/v].

ACKNOWLEDGEMENTS

This research was funded by the "Fond National de la Recherche Scientifique" (Projet de Recherche #23592988) for the Laboratory of Rheumatology and the Laboratory for the Analysis of Medicines, ULg, Liege.

TABLE 1

Regression models: related accuracy and trueness indexes and dosing ranges

| | Accuracy Index | Trueness Index | Dosing range (ng/mL) |
|---|---|---|---|
| Model for C3f | | | |
| Weighted $1/x^2$ quadratic regression | 0.8392 | 0.9782 | 2.50-200.0 |
| Weighted $1/x$ quadratic regression | 0.7923 | 0.8976 | 27.53-200.0 |
| Weighted $1/x^2$ linear regression | 0.6966 | 0.7621 | 21.43-140.1 |
| Weighted $1/x$ linear regression | 0.6285 | 0.4528 | 30.06-200.0 |
| Model for vitronectin fragment | | | |
| Weighted $1/x$ quadratic regression | 0.8649 | 0.9880 | 2.50-100.0 |
| Weighted $1/x^2$ quadratic regression | 0.8609 | 0.9872 | 2.57-100.0 |
| Weighted $1/x^2$ linear regression | 0.8106 | 0.9927 | 2.82-100.0 |
| Weighted $1/x$ linear regression | 0.7990 | 0.9821 | 3.90-100.0 |

TABLE 2

A) C3f and B) vitronectin fragments quantitation - method validation: trueness, precision, accuracy and linearity properties

A. C3f fragment quantitation - Method Validation

| Response function ($k = 3$) | Weighted quadratic regression model calibration range (m = 7): 2.5-200 ng/mL | | |
|---|---|---|---|
| | Series 1 | Series 2 | Series 3 |
| Quadratic term | 0.0001165 | 0.00009036 | 0.00008730 |
| Slope | 0.03261 | 0.02053 | 0.03655 |
| Intercept | −0.3955 | −0.02173 | −0.04982 |
| Weight | $1/x^2$ | $1/x^2$ | $1/x^2$ |
| $r^2$ | 0.9909 | 0.9924 | 0.9885 |

| Trueness ($k = 3$, $n = 2$) (ng/mL) | Relative bias (%) |
|---|---|
| 2.5 | 7.949 |
| 5.0 | 2.060 |
| 10 | −5.575 |
| 20 | 2.715 |
| 50 | 4.251 |
| 100 | 3.443 |
| 200 | −1.307 |

| Precision ($k = 3$, $n = 2$) (ng/mL) | Repeatability (RSD %) | Intermediate precision (RSD %) |
|---|---|---|
| 2.5 | 7.01 | 7.39 |
| 5.0 | 12.09 | 14.80 |
| 10 | 8.54 | 8.74 |
| 20 | 6.16 | 13.02 |
| 50 | 5.59 | 5.59 |
| 100 | 1.61 | 5.76 |
| 200 | 4.41 | 8.82 |

| Accuracy ($k = 3$, $n = 2$) (ng/mL) | ß-expectation tolerance limits (%) | Risk (%) |
|---|---|---|
| 2.5 | [−4.08, 19.97] | 2.56 |
| 5.0 | [−23.22, 27.34] | 14.50 |
| 10 | [−19.68, 8.53] | 3.36 |
| 20 | [−22.89, 28.32] | 15.61 |
| 50 | [−4.72, 13.22] | 0.57 |
| 100 | [−8.62, 15.51] | 4.06 |
| 200 | [−8.38, 5.77] | 0.18 |

| Linearity ($k = 3$, $n = 2$) (ng/mL) | |
|---|---|
| Range | 2.5-200 |
| Slope | 0.9922 |
| Intercept | 0.8931 |
| $r^2$ | 0.9962 |
| LOD | 0.76 |
| LLOQ | 2.5 |

B. Vitronectin fragment quantitation - Method validation

| Response function ($k = 3$) | Weighted quadratic regression model calibration range (m = 6): 2.5-100 ng/mL | | |
|---|---|---|---|
| | Series 1 | Series 2 | Series 3 |
| Quadratic term | 0.0001232 | −0.00001847 | 0.00002566 |
| Slope | 0.05878 | 0.07712 | 0.06873 |
| Intercept | 0.06105 | 0.01201 | 0.02518 |
| Weight | $1/x$ | $1/x$ | $1/x$ |
| $r^2$ | 0.9957 | 0.9673 | 0.9905 |

| Trueness ($k = 3$, $n = 2$) (ng/mL) | Relative bias (%) |
|---|---|
| 2.5 | 2.425 |
| 5.0 | 5.496 |
| 10 | 1.250 |
| 20 | −1.875 |
| 50 | 3.130 |
| 100 | −3.690 |

| Precision ($k = 3$, $n = 2$) (ng/mL) | Repeatability (RSD %) | Intermediate precision (RSD %) |
|---|---|---|
| 2.5 | 8.53 | 14.48 |
| 5.0 | 6.74 | 6.74 |
| 10 | 10.52 | 10.52 |
| 20 | 7.39 | 7.91 |
| 50 | 5.85 | 5.99 |
| 100 | 3.56 | 3.94 |

| Accuracy ($k = 3$, $n = 2$) (ng/mL) | ß-expectation tolerance limits (%) | Risk (%) |
|---|---|---|
| 2.5 | [−24.77, 29.62] | 17.11 |
| 5.0 | [−5.31, 16.30] | 1.32 |
| 10 | [−15.63, 18.13] | 4.83 |
| 20 | [−14.81, 11.06] | 2.15 |
| 50 | [−6.54, 12.80] | 0.74 |
| 100 | [−10.20, 2.82] | 0.19 |

| Linearity ($k = 3$, $n = 2$) (ng/mL) | |
|---|---|
| Range | 2.5-100 |
| Slope | 0.9677 |
| Intercept | 0.6698 |
| $r^2$ | 0.9954 |

TABLE 2-continued

A) C3f and B) vitronectin fragments quantitation - method validation: trueness, precision, accuracy and linearity properties

| | |
|---|---|
| LOD | 0.76 |
| LLOQ | 2.5 | k: Number of days of experiments (series); m: number of concentration levels; n: number of replicates per concentration level and per series.

The invention claimed is:

1. A method, comprising
obtaining a biological sample from a subject that has or is suspected of having an immune-mediated inflammatory disease; and
quantifying simultaneously (a) a V65 vitronectin or fragment, variant or degradation product thereof and (b) a complement C3f or fragment, variant or degradation product thereof by LC/MS-MS analysis of said biological sample, wherein quantifying comprises:
(i) mixing the biological sample with an acidic aqueous solution comprising trifluoro acetic acid (TFA);
(ii) loading the resulting mixture on a trapping LC column;
(iii) eluting the column with an alcoholic mixture and obtaining an eluate;
(iv) drying the eluate;
(v) dispersing the dried eluate in an acetonitrile aqueous solution;
(vi) loading the resulting dispersion on a reversed phase LC column and separating two mobile phases; and
(vii) injecting by continuous flux in MS-MS, both mobile phases and simultaneously quantifying the V65 vitronectin or fragment, variant or degradation product thereof and the complement C3f or fragment, variant or degradation product thereof.

2. The method according to claim 1, wherein the subject is a human.

3. The method according to claim 1, wherein the biological sample is blood, serum, plasma, urine, or synovial fluid.

4. The method according to claim 1, wherein the V65 vitronectin fragment comprises the following amino sequence: SQRGHSRGRNQNSRRPS (SEQ ID NO:1).

5. The method according to claim 1, wherein the complement C3f comprises the following amino sequence: SSKITHRIHWESASLLR (SEQ ID NO:2).

6. The method according to claim 1, wherein the immune-mediated inflammatory diseases is osteoarthritis.

7. The method according to claim 1, wherein the immune-mediated inflammatory diseases is lupus.

8. The method according to claim 1, wherein the immune-mediated inflammatory diseases is sclerodermia.

9. The method according to claim 1 wherein the LC/MS-MS analysis comprises microfluidic liquid chromatography coupled to a nanoelectrospray source ion trap mass spectrometry analysis.

10. The method according to claim 1, wherein the acidic aqueous solution comprises 1% v trifluoro acetic acid (TFA).

11. The method according to claim 1, wherein the alcoholic mixture is methanol/water/TFA.

12. The method according to claim 11, wherein the mixture methanol/water/TFA is in a ratio from 90:7:3 to 90:9:1 v/v/v.

13. The method according to claim 1, wherein the acetonitrile aqueous solution comprises TFA.

14. The method according to claim 13, wherein the acetonitrile aqueous solution comprising TFA is in a ratio acetonitrile/water/TFA from 3:97:0.1 to 1:99:0.1 v/v/v.

15. The method according to claim 1, wherein the complement C3f or fragment, variant or degradation product thereof are quantified at m/z 459.3, 530.7 and 646.3 and wherein the V65 vitronectin or fragment, variant or degradation product thereof are quantified at m/z 434.9, 445.2, 460.5, 466.2, 469.7, 480.3, 485.3.

16. The method according to claim 11, wherein the mixture methanol/water/TFA is in a ratio of 90:9:1 v/v/v.

17. The method according to claim 13, wherein the acetonitrile aqueous solution comprising TFA is in a ratio acetonitrile/water/TFA of 1:99:0.1 v/v/v.

18. The method according to claim 1, wherein the trapping LC column is washed prior to eluting the column.

* * * * *